(12) United States Patent
Stratis et al.

(10) Patent No.: US 9,719,924 B1
(45) Date of Patent: Aug. 1, 2017

(54) WIDEBAND ANTENNA STRUCTURE WITH OPTICS REFLECTOR AS GROUND PLANE AND ASSOCIATED METHODS

(71) Applicant: Raytheon Company, Waltham, MA (US)

(72) Inventors: Glafkos K. Stratis, Tucson, AZ (US); David J. Knapp, Tucson, AZ (US); Douglas Mills, Tucson, AZ (US); Raymond A. Graffam, Tucson, AZ (US); Michael S. Smith, Oro Valley, AZ (US)

(73) Assignee: Raytheon Company, Waltham, MA (US)

( * ) Notice: Subject to any disclaimer, the term of this patent is extended or adjusted under 35 U.S.C. 154(b) by 253 days.

(21) Appl. No.: 14/550,407

(22) Filed: Nov. 21, 2014

(51) Int. Cl.
| | |
|---|---|
| *G01N 21/00* | (2006.01) |
| *G01N 21/64* | (2006.01) |
| *G01N 21/68* | (2006.01) |
| *G01N 15/10* | (2006.01) |
| *G01J 3/02* | (2006.01) |

(52) U.S. Cl.
CPC ............. *G01N 21/64* (2013.01); *G01N 21/68* (2013.01); *G01J 3/02* (2013.01); *G01N 2015/1037* (2013.01)

(58) Field of Classification Search
CPC ... H01J 37/32935; G01N 21/64; G01N 21/68; G01N 2015/1037; G01J 3/02
See application file for complete search history.

(56) References Cited

U.S. PATENT DOCUMENTS

| | | | | |
|---|---|---|---|---|
| 5,182,564 A | * | 1/1993 | Burkett | F41G 7/008 342/53 |
| 5,394,163 A | | 2/1995 | Bullen et al. | |

FOREIGN PATENT DOCUMENTS

GB  2510162 A  7/2014

OTHER PUBLICATIONS

PCT Search Report and Written Opinion of ISA; for PCT Pat. App. No. PCT/US2015/050895; 16 pages.
Veereshappa et al., "Pentagon and Circular Ring Slot Loaded Rectangular Microstrip Monopole Antennas for Quad-Band Operation"; *IJECET* Apr. 30, 2013, pp. 151-157 (7 pages).
PCT International Search Report and Written Opinion of the ISA dated Nov. 26, 2015; For PCT Pat. App. No. PCT/US2015/050897; 17 pages.
Li et al; "A Unidirectional Cylindrical Conformal Monopole Antenna Designed for Impulse Radar System;" IEEE Antennas and Wireless Propagation Letters, vol. 10, Jan. 2011; pp. 1397-1400 (4 pages).

(Continued)

*Primary Examiner* — Abdullahi Nur
(74) *Attorney, Agent, or Firm* — Daly, Crowley, Mofford & Durkee, LLP

(57) ABSTRACT

A compact transducer system includes both an antenna subsystem and an optical transducer subsystem. The antenna subsystem may include multiple radio frequency (RF) radiating elements disposed adjacent to a ground plane. The ground plane may also serve as an optical reflector within an optical path of the optical transducer subsystem. A secondary reflector may also be provided within the optical path of the optical transducer subsystem. The secondary reflector may be formed of dielectric material (e.g., meta-material) in some embodiments to prevent undesired coupling with RF circuitry.

21 Claims, 18 Drawing Sheets

(56) References Cited

OTHER PUBLICATIONS

Modi et al; "An Ultra Wideband Vertical Slotted Orthogonal Semi Elliptical Sheets Monopole Antenna with Finite Ground Plane;" International Journal of Scientific and Engineering Research, vol. 3, issue 10, Oct. 2012; 4 pages.

Shafal, L., Latif, S., & Shafal, C. (Apr. 2013). Loss reduction in planar circuits and antennas over a ground plane using engineered conductors. In *Antennas and Propagation (EuCAP), 2013 7th European Conference on* (pp. 1031-1035). IEEE.

U.S. Appl. No. 14/550,529, filed Nov. 21, 2014, Stratis et al.

* cited by examiner

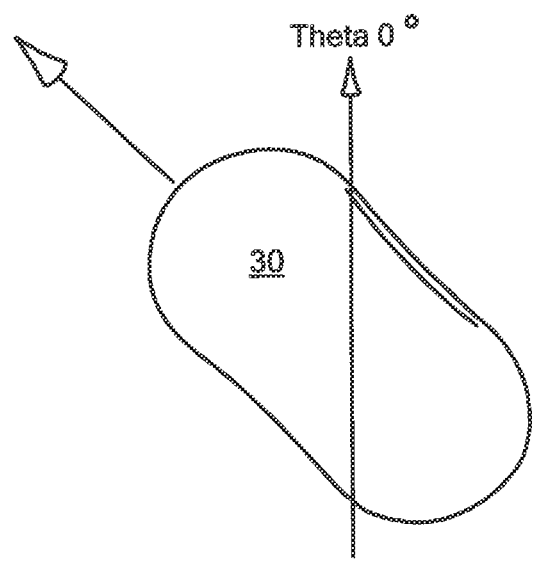
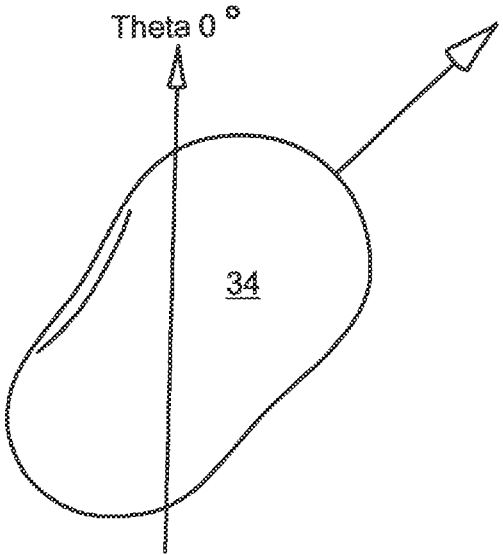
FIG. 3A    FIG. 3B
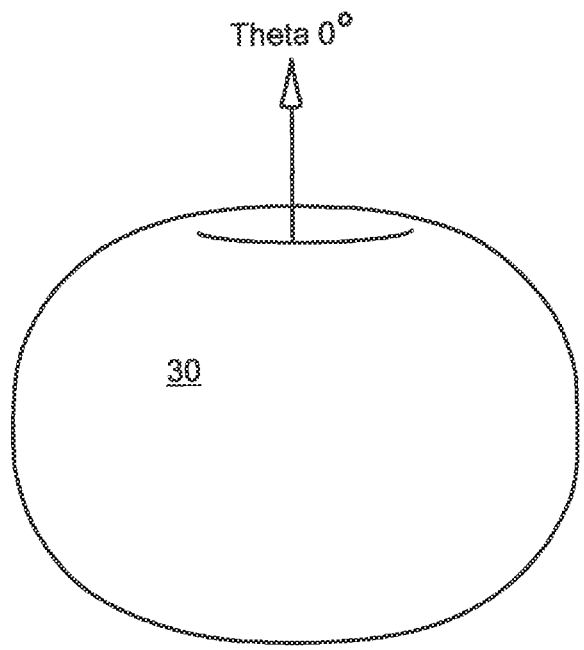
FIG. 3C

WIDEBAND ANTENNA STRUCTURE WITH OPTICS REFLECTOR AS GROUND PLANE AND ASSOCIATED METHODS

BACKGROUND

An antenna is a radio frequency (RF) transducer device that can act as a transition between an RF transmission line and free space propagation. As such, an antenna can be used to transmit RF signals into free space or receive signals therefrom. An ongoing trend in the wireless industry is to create smaller and smaller devices and systems for use in communications and other wireless applications. Military wireless applications are also trending toward smaller devices and platforms for RF systems. At the same time, the demand for system bandwidth is increasing in both commercial and military systems. There is also a desire to add further functionality to RF systems for performing additional tasks. It is often desired that this additional functionality be added without a corresponding increase in system size. This can require the collocation of different types of radiating systems within a given small volume.

SUMMARY

Antenna structures and combined optical/RF transducer systems are disclosed that are capable of implementation within a small physical volume. In some implementations, the antenna structures are capable of wideband RF performance. For example, in one embodiment, a compact antenna structure provides a return loss of −6 db or better across an ultrawideband (UWB) operational frequency range from 0.65 GHz to almost 5 GHz. In this embodiment, the antenna is implemented in a volume defined by a cylinder having a diameter of 2.75 inches. As will be appreciated, this is a very small space for an antenna operative at 0.65 GHz. Because the antenna structures and combined optical/RF transducer systems are capable of compact implementation, they are well suited for use in applications having limited available space (e.g., missile systems, aircraft, small devices, cell towers, and other small platforms). The wide RF frequency range capabilities of the antennas can support multiple RF applications at the same time, including, for example, communications, global positioning system (GPS) support, radar tracking, radar guidance, and/or others.

In some embodiments, a transducer system is provided that includes an antenna subsystem and a collocated optical transducer subsystem. The antenna subsystem may include multiple RF radiating elements disposed adjacent to a ground plane. In some implementations, the multiple radiating elements may include monopole elements that are located near edges of the ground plane. Any number of elements may be used.

In various embodiments, the ground plane of the antenna subsystem may also act as an optical reflector within the optical transducer subsystem. To act as an optical reflector, the ground plane may be processed in some manner to make it more reflective (e.g., polishing, reflective layer applied, etc.). The shape of the ground plane may also be adapted for use as a reflector. For example, in some embodiments, a parabolic shape is used. Other shapes may alternatively be used. In some prior systems that combined RF and optical transducer systems (e.g., SDB II, etc.), antenna structures with ground planes were implemented within a primary reflector of the corresponding optical system. This approach placed limits on the bandwidth that was achievable by the RF antenna structures, particularly limits on low frequency operation. By using a ground plane that also acts as an optical reflector, as described herein, many of the bandwidth limits associated with prior systems are removed, thus allowing relatively wide RF bandwidth in the presence of the optical subsystem.

The ground plane/optical reflector described above, may be part of an optical path within the optical transducer subsystem. In some embodiments, a secondary optical reflector may also be provided within the optical path. The secondary optical reflector and the primary optical reflector may be arranged to operate, for example, like a Cassegrain antenna in some implementations. In some embodiments, the ground plane may include an opening in a central portion thereof through which optical signals and/or equipment may pass. In some embodiments, the secondary optical reflector may be configured to focus light through this opening during light signal reception operations, to be detected by an optical detector behind the ground plane. In some implementations, the secondary reflector may be formed from dielectric material so that it has less effect on the RF circuit operation. For example, in some embodiments, the secondary optical reflector may be located between two or more of the RF radiating elements in the systems. By using dielectric reflectors, coupling with the RF radiating elements may be minimized. In at least one approach, meta-materials may be used for the secondary reflector.

In accordance with one aspect of the concepts, systems, circuits, and techniques described herein, a transducer system comprises: an antenna subsystem including multiple radio frequency (RF) radiating elements disposed adjacent to a ground plane; and an optical transducer subsystem collocated with the antenna subsystem, wherein the ground plane is an optical reflector in the optical transducer subsystem in addition to being a ground plane in the antenna subsystem.

In one embodiment, the ground plane includes an opening in a central region thereof; and the optical transducer subsystem extends through the opening in the ground plane.

In one embodiment, the multiple RF radiating elements include first and second monopole radiating elements located near opposing edges of the ground plane.

In one embodiment, the optical transducer subsystem includes an optical source to generate a light signal, an optical element to transmit the light signal into an exterior environment, and an optical path coupling the optical source and the optical element, wherein the ground plane is an optical reflector within the optical path.

In one embodiment, the ground plane is a primary optical reflector within an optical path of the optical transducer subsystem; and the optical transducer subsystem further comprises a secondary optical reflector within the optical path that is different from the primary optical reflector.

In one embodiment, the secondary optical reflector is formed of dielectric material.

In one embodiment, the secondary optical reflector is formed of meta-material.

In one embodiment, the multiple RF radiating elements include first and second monopole radiating elements located near opposing edges of the ground plane; and the secondary optical reflector is located in a region between the first and second monopole radiating elements, wherein the secondary optical reflector provides little or no coupling with the first and second monopole radiating elements.

In one embodiment, the ground plane includes an opening in a central region thereof; and the secondary reflector is positioned to focus light signals through the opening in the ground plane during light signal reception operations.

In one embodiment, the ground plane has either a parabolic shape or a semi-spherical shape.

In one embodiment, the ground plane is highly polished.

In one embodiment, the ground plane has a highly reflective coating.

In one embodiment, the multiple RF radiating elements include first and second monopole radiating elements located near opposing edges of the ground plane; and the first and second monopole radiating elements each include an opening therein for use as an optical aperture.

In one embodiment, the transducer system is located within a missile.

In one embodiment, the multiple RF radiating elements include first and second monopole radiating elements located near opposing edges of the ground plane; and the first and second monopole radiating elements are conformal to a surface of a radome.

In accordance with another aspect of the concepts, systems, circuits, and techniques described herein, a transducer system comprises: (a) an antenna subsystem including: (i) a ground plane having an opening in a central region thereof; and (ii) multiple radio frequency (RF) radiating elements disposed adjacent to the ground plane; and (b) an optical transducer subsystem collocated with the antenna subsystem, the optical transducer subsystem including a secondary reflector configured to reflect light signals toward the opening in the ground plane or reflect light signals received through the opening in the ground plane during optical operations.

In one embodiment, the secondary reflector is located between at least two of the RF radiating elements of the antenna subsystem and is formed of dielectric material to prevent significant coupling with the at least two RF radiating elements.

In one embodiment, the secondary reflector includes meta-material.

In one embodiment, the ground plane is a primary optical reflector in an optical path associated with the optical transducer subsystem in addition to being a ground plane in the antenna subsystem.

In one embodiment, the ground plane has either a parabolic shape or a semi-spherical shape.

BRIEF DESCRIPTION OF THE DRAWINGS

The foregoing features may be more fully understood from the following description of the drawings in which:

FIGS. 3A and 3B are diagrams illustrating tilted radiation patterns associated with monopole radiating elements disposed on or near an edge of a circular ground plane;

FIG. 3C is a diagram illustrating a composite radiation pattern formed by combining the patterns of FIGS. 3A and 3B;

DETAILED DESCRIPTION

Radio frequency (RF) antenna and combined RF and optical transducer systems are disclosed that are capable of implementation within a relatively small, compact region. In various embodiments, systems having wide bandwidths are provided. As will be described in greater detail, in various embodiments, ground planes are provided that may be shared amongst various applications being implemented within a confined space. As used herein, the phrase "ground plane" is defined in the broader sense of a grounded electrically conductive surface that is not necessarily limited to a particular shape, such as a flat planar shape (although flat planar ground planes are used in some embodiments).

Figure 1:
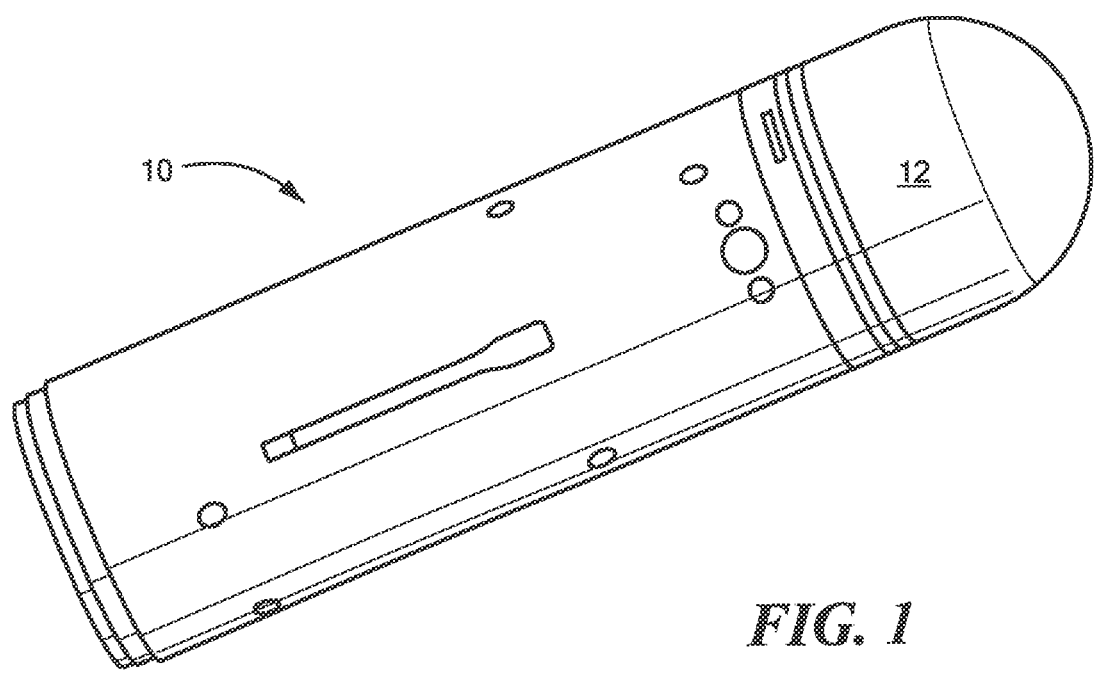
FIG. 1 is a diagram illustrating a missile that may include a transducer system in accordance with an embodiment.

There are many RF applications where space for implementing transmission and/or reception equipment is limited. These applications include, for example, RF systems for missiles and other projectiles, RF systems for aircraft, RF systems for small handheld devices, cell towers, RF systems for laptop, tablet, and desktop computers, wireless security systems with optical/RF, and others. FIG. 1 is a diagram illustrating an exemplary missile 10 that may include RF transmission and reception equipment in accordance with an embodiment. This equipment may be used, for example, for missile target tracking and guidance functions. Typically, in a missile application, some or all of the RF equipment may be implemented in or near the nosecone 12 at the front of the missile 10. For example, the nosecone 12 may include one or more antennas for the RF systems on board. A problem with this is that many modern missiles are small in size with very limited space. Many missiles, for example, have diameters of only a few inches, leaving little room for internal systems. This problem is exacerbated by the fact that many modern RF systems are requiring greater and greater operational bandwidths, including bandwidths that extend to lower frequencies. As is well known, antennas that are operative at lower frequencies are typically larger in size than higher frequency antennas. Thus, it is difficult to design antennas for lower frequency applications that fit in small volumes. As will be described in greater detail, antenna systems and techniques are provided herein that are capable of compact implementation while providing relatively broadband operation. In some embodiments, hybrid RF/optical transducer systems are provided that are also capable of compact implementation. In the discussion that follows, antenna systems and hybrid systems will be described in the context of a missile implementation. It should be appreciated, however, that many of the concepts, features, structures, systems, and techniques described herein also have use in various other applications.

Figure 2:
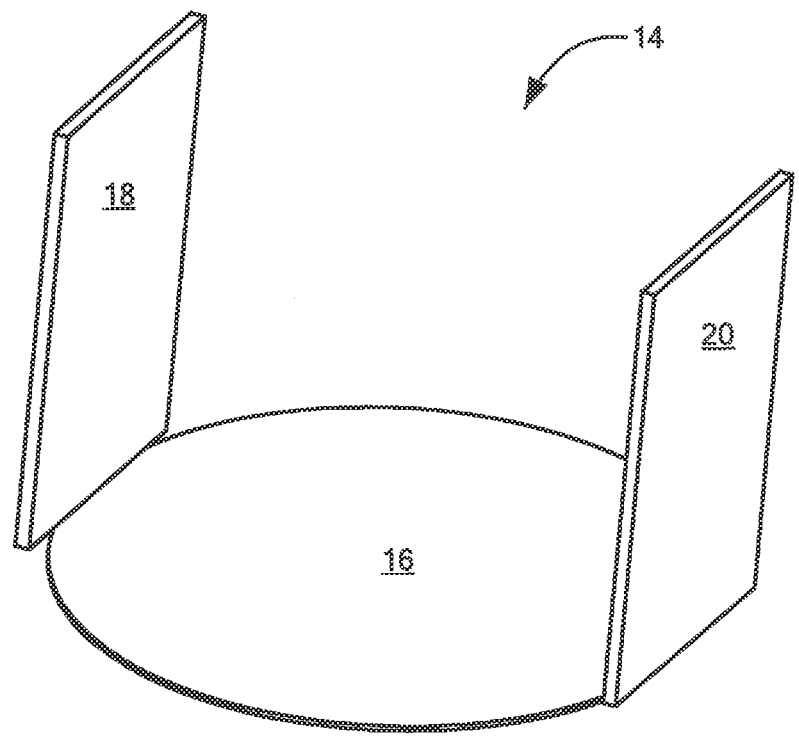
FIG. 2 is a diagram illustrating an exemplary antenna system in accordance with an embodiment.

FIG. 2 is a diagram illustrating an exemplary antenna 14 in accordance with an embodiment. As shown, the antenna 14 includes a ground plane 16 and first and second monopole radiating elements 18, 20. Other types of radiating elements may be used in other implementations including, for example, half bow tie elements, half Z monopole elements, and/or others. The monopole elements 18, 20 may each be located near an outer edge of the ground plane 16, on opposite sides thereof. As shown in FIG. 2, the monopole elements 18, 20 may be oriented in a perpendicular or near perpendicular direction with respect to the ground plane 16 in some embodiments. However, other orientations are also possible. Both elements 18, 20 use the ground plane 16 to facilitate transmission and/or reception of RF signals to/from a surrounding wireless environment. The monopole elements 18, 20 may be fed by, for example, coaxial cable feeds extending through the ground plane 16 or in some other manner. In at least one implementation, it was found that the arrangement of FIG. 2 was capable of achieving a relatively wide operational bandwidth in a relatively compact form. For example, in one implementation, an operational bandwidth from approximately 0.65 GHz to approximately 5 GHz was achieved within a nosecone diameter of 2.75 inches using rectangular monopole elements of approximately 0.8×2.8 inches.

In a conventional monopole arrangement, a single monopole element is situated above a ground plane in a central region thereof. The ground plane forms an image of the monopole which combines with the monopole itself to form a radiation pattern similar to that of a dipole. In conceiving the antenna structure 14 of FIG. 2, it was determined that a monopole element could be moved outwards toward an edge of a ground plane and still be useable. It was also found that at least one additional monopole element could be added at one or more other edge locations around the ground plane. Signal processing can be used to achieve a desired total radiation pattern using multiple monopoles in the above-described arrangement.

FIG. 3A is a diagram illustrating an exemplary radiation pattern 30 of a single monopole radiating element disposed above a circular ground plane near an edge thereof. As shown, the radiation pattern is essentially a tilted version of a conventional monopole pattern, with a little shape distortion. FIG. 3B is a diagram illustrating a similar tilted radiation pattern 32 associated with a monopole radiating element disposed near the edge on an opposite side of the circular ground plane. As shown, the shape is substantially the same, but the pattern is tilted in the opposite direction. Using signal processing, the two patterns can be combined to achieve a desired composite pattern for the antenna. For example, in some missile systems, an RF null is desired in the direction of movement of the missile. In such a system, the two beams 30, 32 of FIGS. 3A and 3B can be combined using appropriate phasing (e.g., 90 degree phase difference) to generate the composite pattern 34 of FIG. 3C having a null in the direction of movement. Different phasing may be used to achieve other composite patterns (e.g., a pattern with a maximum in the direction of travel of the missile, etc.).

As described above, in the illustrated embodiment, two monopole elements 18, 20 are located near an edge of a ground plane 16 on opposite sides thereof. In other embodiments, one or more additional pairs of opposing monopole elements may be added to the antenna arrangement 14 of FIG. 2. Each pair of elements may increase the ability of the antenna 14 to find and/or track targets-of-interest about a missile. The more elements that are used, the more targets can be simultaneously identified. Furthermore, the use of additional elements also increases the ability of the system to support adaptive diversity techniques (e.g., spatial diversity, polarization diversity, beamforming, etc.). In some embodiments, the different pairs of elements are distributed at equal angular intervals about the circumference of the ground plane 16. For example, in one embodiment, two pairs of monopole elements are used, with one element at each 90 degree interval about the ground plane 16. In another embodiment, three pairs of elements are used, with one element every 60 degrees, and so on. In some embodiments, radiating elements are not grouped in pairs.

In various implementations, signal processing circuitry may be provided to process signals received by or delivered to the various monopole elements to achieve one or more desired results. For example, as described above, in some implementations, digital or conventional beamforming techniques may be used to process signals associated with all or selected subgroups (e.g., pairs) of elements to achieve a desired antenna pattern. Other processing techniques may also, or alternatively, be used including, for example, MIMO techniques, monopulse techniques, location finding techniques using scalar sensors or vector sensors (polarization), radar applications, reconfigurable arrays, and/or others.

Figure 4:
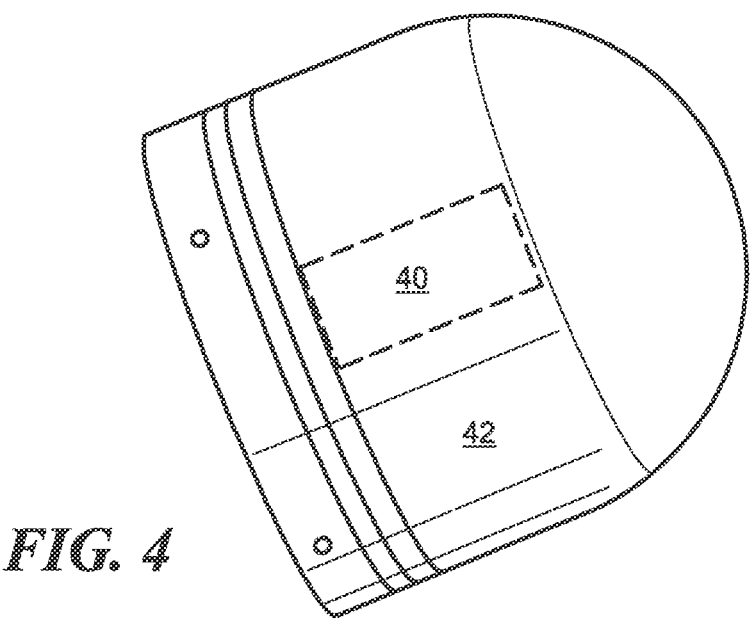
FIG. 4 is a diagram illustrating an approximately rectangular monopole radiating element disposed on an inner surface of a missile radome in accordance with an embodiment.
Figure 5:
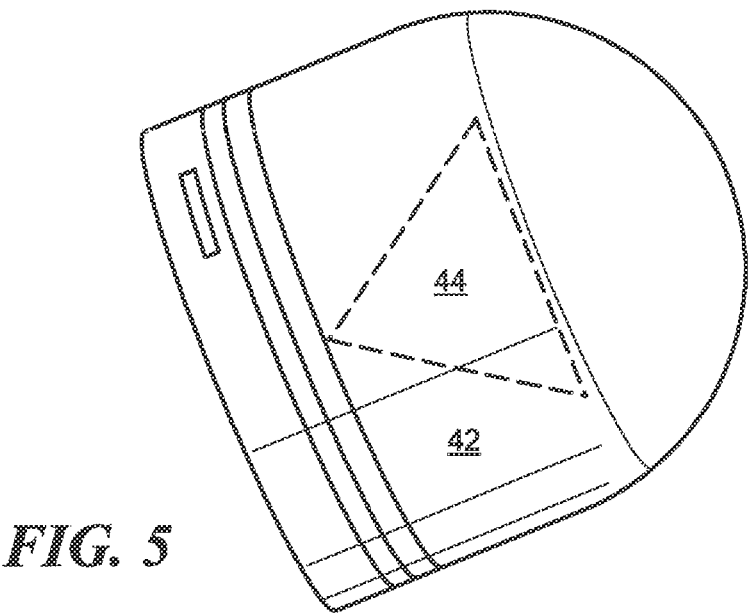
FIG. 5 is a diagram illustrating an approximately triangular monopole radiating element disposed on an inner surface of a missile radome in accordance with an embodiment.

Referring back to FIG. 2, in at least one embodiment, the monopole elements 18, 20 may be conformal to an interior or exterior surface of a radome forming the nosecone of a missile. Using this approach, the least possible interior space within the nosecone is consumed by the monopole elements. FIG. 4 is a diagram illustrating an approximately rectangular monopole element 40 disposed on an inner surface of a radome 42 of a missile. Because the monopole element 40 is conformal to the surface of the radome, it may be a three dimensional structure and not a two dimensional rectangle. Similar elements may be disposed at other angular locations on the radome 42. Other element shapes may also be used. For example, FIG. 5 shows a triangular monopole element 44 on an inner surface of a radome 42. The radome 42 may be formed of a very low loss, high strength dielectric material (e.g., quartz, fused silica, ceramic materials, silicon nitride, and/or others).

Figure 6:
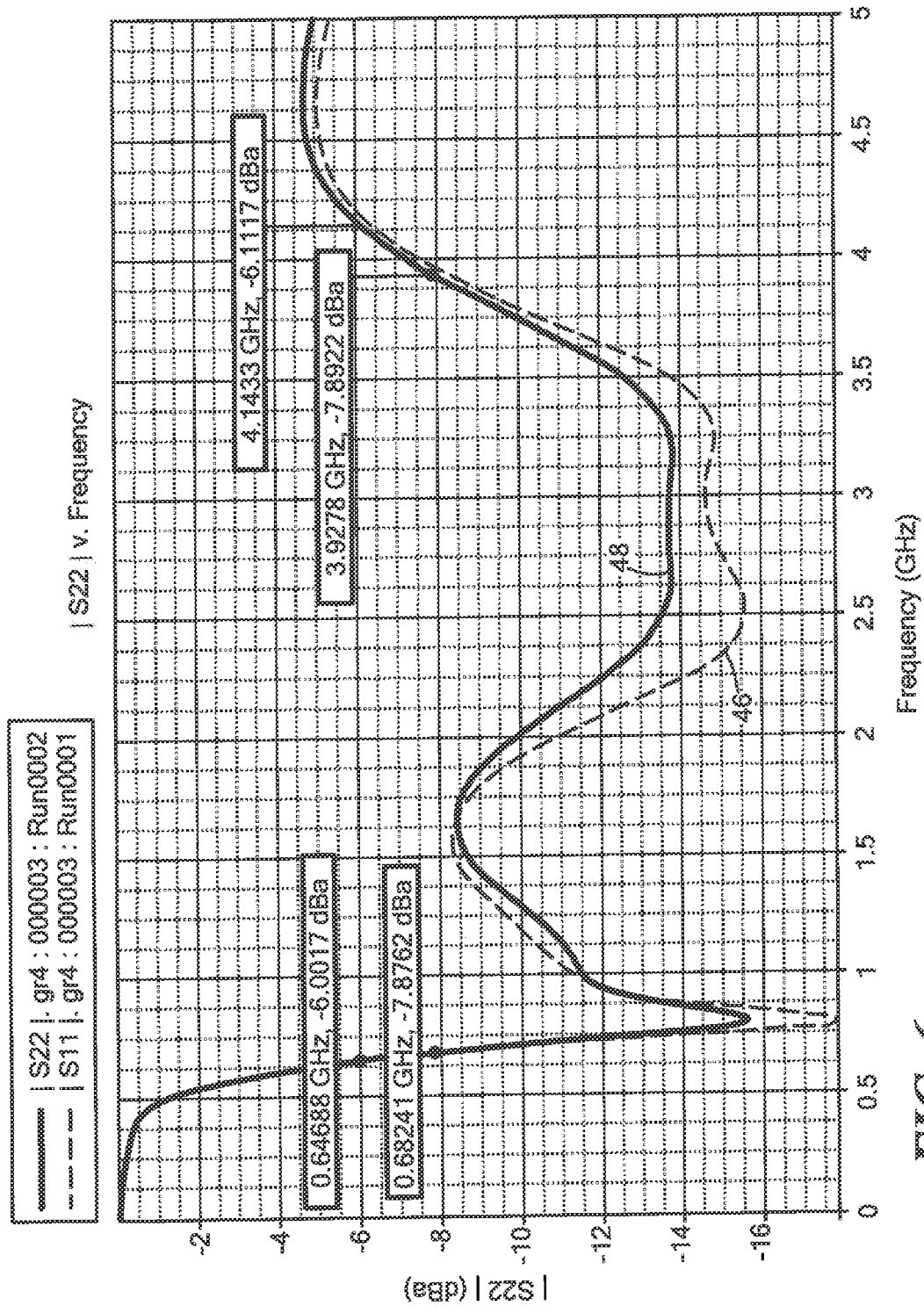
FIG. 6 is a plot illustrating simulated return loss as a function of frequency for the antenna of FIG. 2.

FIG. 6 is a plot illustrating exemplary return loss simulation results for the monopole elements 18, 20 of the antenna 14 of FIG. 2. To test the potential effect of radome mounting, monopole element 20 was adhered to a layer of quartz material for the test. Monopole element 18 was tested without a quartz layer. Curve 46 in FIG. 6 represents the simulated return loss versus frequency for monopole element 18 (without quartz) and curve 48 represents the simulated return loss versus frequency for monopole element 20 (with quartz). As shown, both elements are capable of providing adequate input return loss over the frequency band of interest. In addition, the reduction in return loss caused by the presence of the quartz is relatively small.

Figure 7:
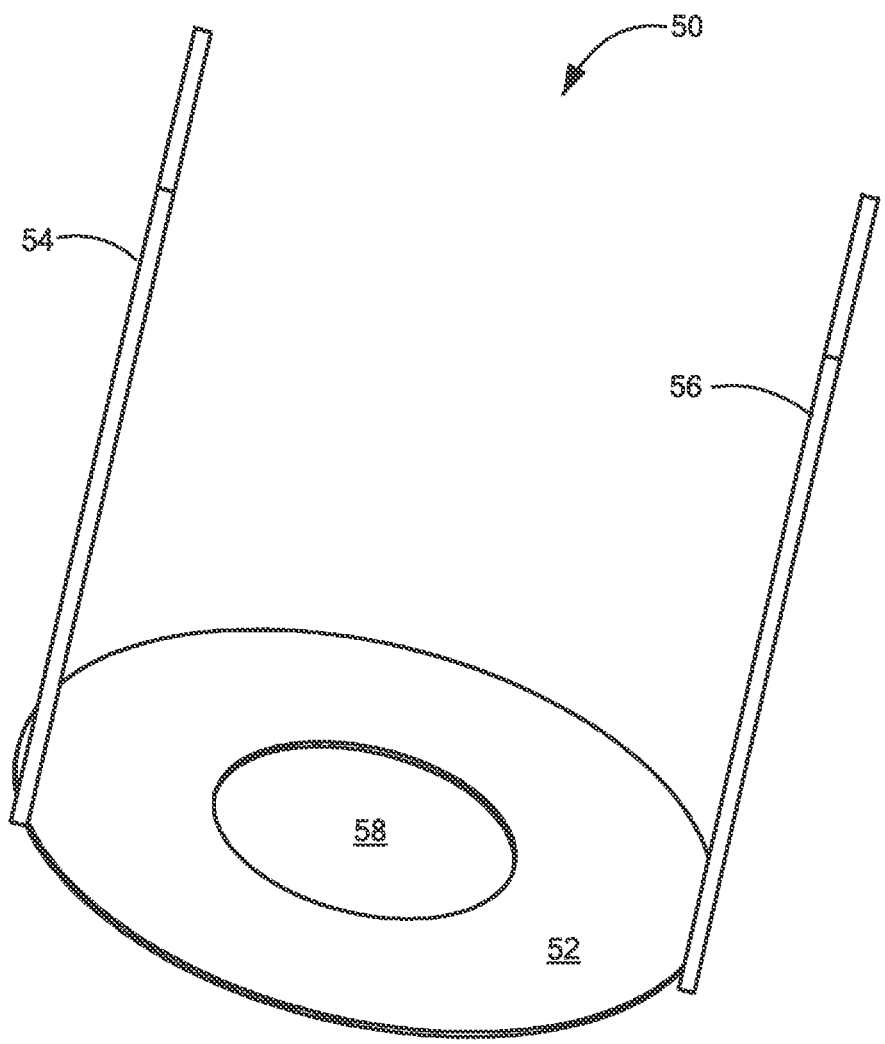
FIG. 7 is a diagram illustrating an exemplary antenna arrangement having an opening in a ground plane for use in implementing a combined RF-optical transducer system in accordance with an embodiment.

In some systems, it may be desirable to add one or more additional transducers to a missile radome to provide additional transmission/reception functionality. For example, in some systems, it may be desirable to add optical equipment to a missile to provide one or more optics-based capabilities. In some embodiments, a combination RF and optical transducer system is provided that includes both RF antenna functionality and optical functionality co-located within a common compact system. FIG. 7 is a diagram illustrating an exemplary antenna arrangement 50 that may be used to provide such a combination system. As shown, the antenna arrangement 50 may include a ground plane 52 and first and second monopole elements 54, 56, as before. However, unlike the antenna 14 of FIG. 2, the ground plane 52 of FIG. 7 includes an opening 58 in a central region thereof through which optical equipment and/or signals may pass for use in performing optical transmission and/or reception applications. It was determined that little or no RF performance degradation would result in the RF antenna if optical elements extended through a central portion of the ground plane 52.

Although not shown in FIG. 7, various different types of optical equipment may be used within a missile and any of this equipment may extend through the opening 58 in the ground plane 52. This may include, for example, optical fiber connecting an optical source behind the ground plane to an optical element (e.g., a lens) in front of the ground plane, optical fiber coupling optical detection circuitry behind the ground plane to an optical element in front of the ground plane 52, lenses, metamaterial lenses, dielectric metamaterials (e.g., window 90 in FIG. 9), dielectric polarizers, optical fibers, bundles of optical fibers, prisms, liquid crystal polarizers, and/or others. The dielectric metamaterial window 90 in FIG. 9 allows the opportunity to see backwards as well (for negative index of refraction metamaterials) for light going through or coming from the back. In various embodiments, unguided light may pass through the opening 58 during normal operation. Various optical devices may be placed just underneath the ground plane to detect or generate such light. In some embodiments, optical fibers, lenses, and other optical structures passing through the opening 58 in the ground plane 52 may be formed of a relatively low loss or lossless dielectric material such as, for example, quartz, fused silica, ceramic materials, silicon nitride, and/or others. Furthermore, layers of these materials combined can introduce new properties (e.g., dielectric metamaterials, etc).

In some embodiments, the above-described approach may allow optical equipment to be added to the nosecone region of a missile with no increase in size of the region. That is, the optical equipment may be collocated with the wideband RF antenna equipment within the same small available space, with little or no degradation in RF performance. It was also found that, within certain limits, the RF antenna performance was not significantly affected by increases in the size of the opening in the ground plane. For example, in one test, the diameter of an opening in a ground plane was doubled from 2 cm to 4 cm with little effect on antenna performance.

Figure 8:
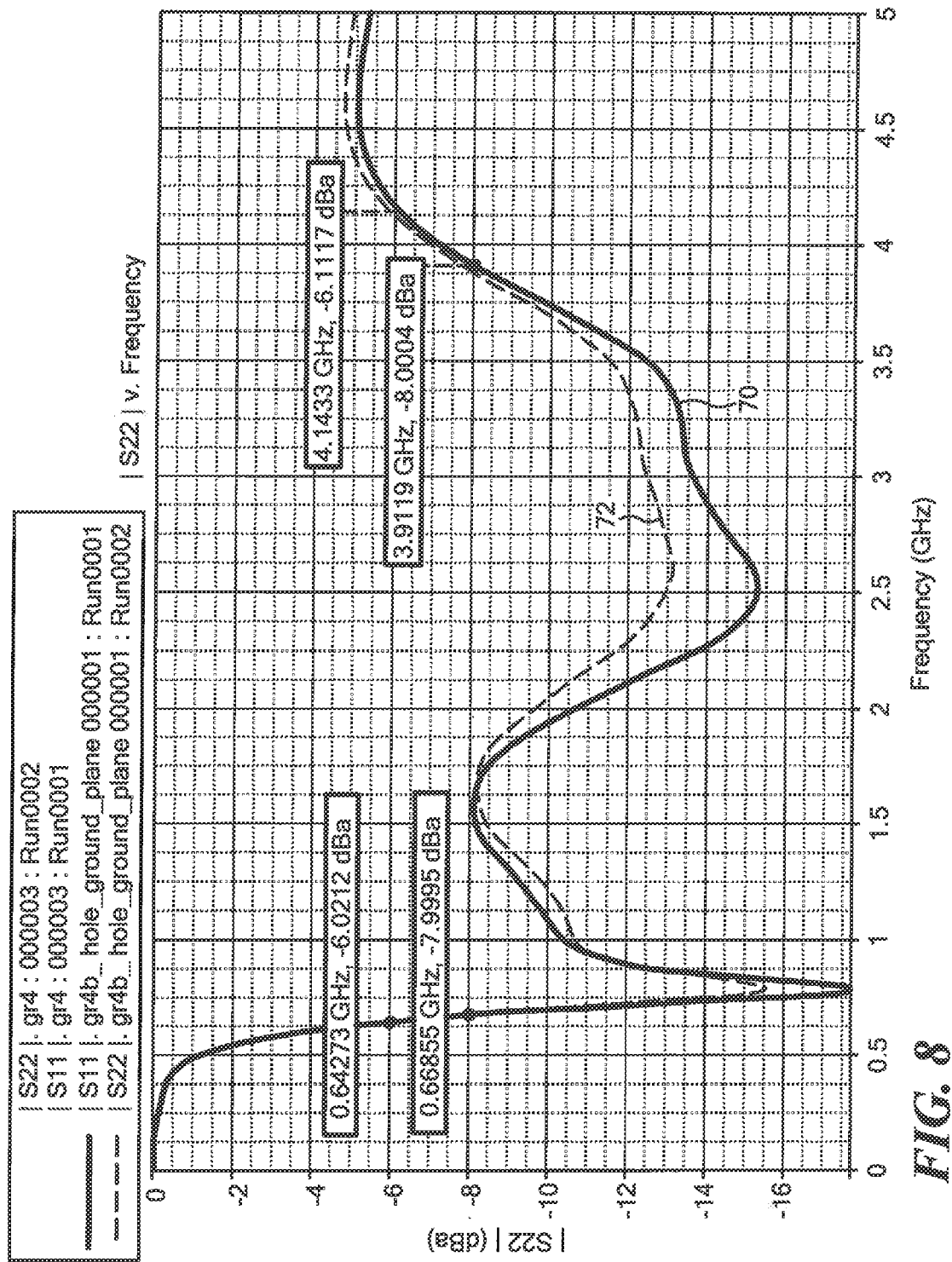
FIG. 8 is a plot illustrating simulated return loss for the antenna of FIG. 7.

FIG. 8 is a plot illustrating simulated return loss versus frequency for the monopole elements 54, 56 of the antenna 50 of FIG. 7 that includes an opening through a corresponding ground plane. As before, one of the elements (i.e., element 56) was adhered to a quartz layer for testing and the other was not. Curve 70 in FIG. 8 represents the simulated return loss versus frequency for monopole element 54 (without quartz) and curve 72 represents the simulated return loss versus frequency for monopole element 56 (with quartz). As before, the reduction in return loss caused by the presence of the quartz is relatively minor. In addition, a comparison of the plot of FIG. 8 to the plot of FIG. 6 shows that the addition of the opening 58 to the ground plane had little effect on RF performance.

Figure 9:
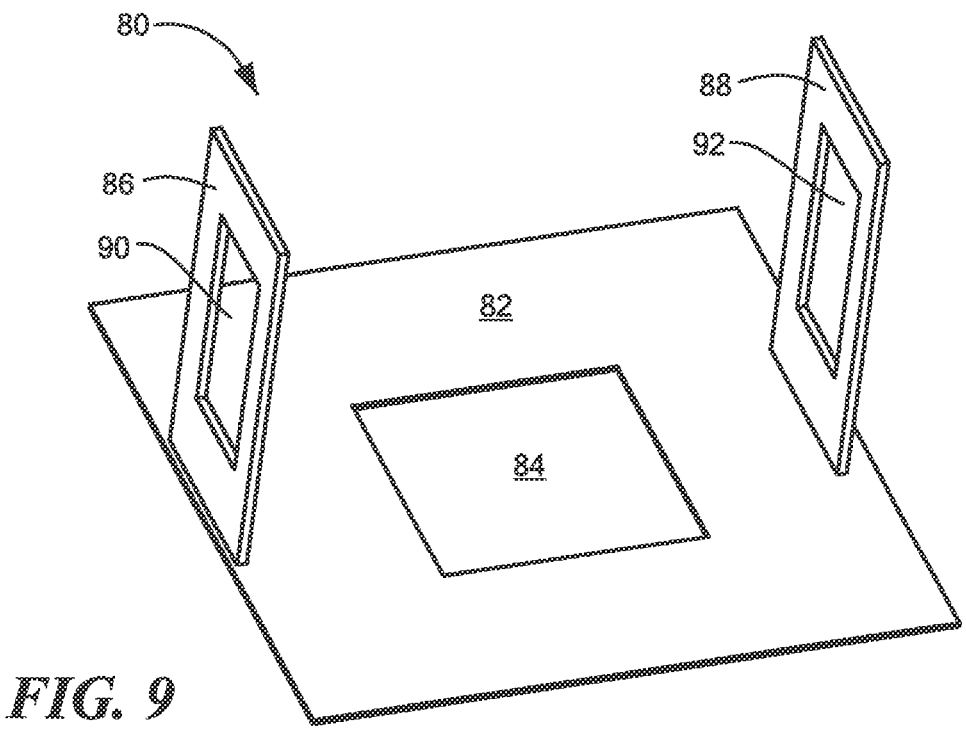
FIG. 9 is a diagram illustrating another exemplary antenna system in accordance with an embodiment.

In the description above, various features and techniques were discussed in the context of a missile application. As described previously, techniques and systems of the present disclosure may be implemented in a wide variety of different applications and are not limited to missile-based implementations. In the previously described embodiments, the ground plane was illustrated as being circular as this shape is well suited for missile applications. However, other ground plane shapes may alternatively be used (e.g., square, rectangular, triangular, etc.). FIG. 9 is a diagram illustrating an exemplary antenna system 80 in accordance with an embodiment that includes a square ground plane. As shown, the antenna system 80 includes a ground plane 82 having an opening 84, and first and second monopole radiating elements 86, 88. The ground plane 82 is square as is the opening 84. Other shapes may alternatively be used. As before, the opening 84 in the ground plane 82 may be used to accommodate optical transducer related equipment or signals to implement a combination RF and optical transducer system. The first and second monopole radiating elements 86, 88 are located near the edges of the ground plane 82, on opposite sides thereof. As described previously, additional monopole radiating elements may be added to the antenna structure 80 at different locations about the edge of the ground plane 82. The first and second monopole radiating elements may be conformal to a radome surface in non-missile applications as well as in missile applications.

As shown in FIG. 9, the monopole radiating elements 86, 88 may each have a corresponding opening 90, 92 through a central portion thereof. As with the opening 84 in the ground plane 82, in some implementations, the openings 90, 92 may be used to accommodate optical equipment or signals. For example, in some implementations, the openings 90, 92 may form optical apertures for the antenna system 80. However, in other implementations, the openings 90, 92 in the monopole elements 86, 88 may be used in a different manner. For example, in some implementations, the openings 90, 92 may be used as secondary RF apertures. For example, a dipole radiating element could be situated within or behind each of the openings 90, 92 in the monopole elements 86, 88 to transmit and/or receive signals in a different frequency band. Other antenna types may alternatively be used. In some embodiments, an array antenna may be implemented within one or more of the openings 90, 92. The antennas implemented within the openings 90, 92 may, in some embodiments, be operative in a frequency band above the highest frequency of the monopole elements 86, 88. In this manner, an even higher overall RF bandwidth can be achieved.

Figure 10:
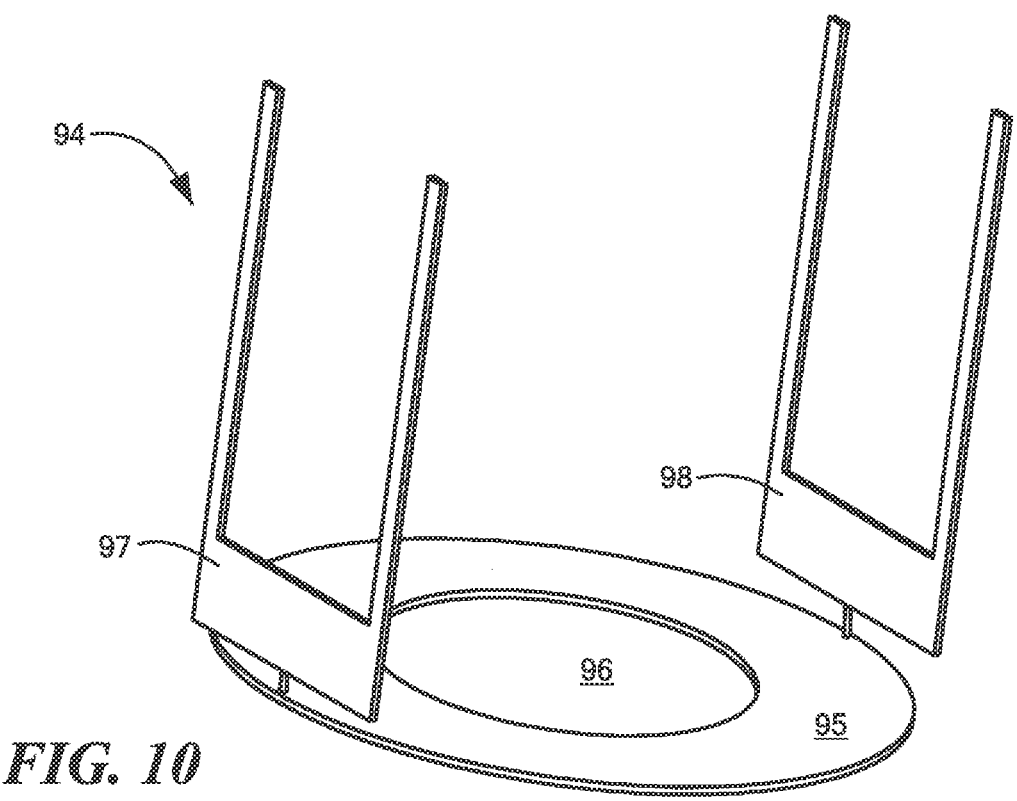
FIG. 10 is a diagram illustrating an exemplary antenna system that represents a modification of the antenna system of FIG. 9 in accordance with an embodiment.

FIG. 10 is a diagram illustrating an exemplary antenna system 94 in accordance with another embodiment. The antenna system 94 represents a modification of the system of FIG. 9. As shown, the antenna system 94 includes a ground plane 95 having an opening 96, and first and second monopole radiating elements 97, 98. The first and second monopole radiating elements 97, 98 have a "goal post" configuration with an opening having an open top. As in the previous embodiment, the opening may be used as an optical aperture or as an additional RF aperture in some embodiments. Additional monopole radiating elements may also be added to the ground plane 95.

Figure 11:
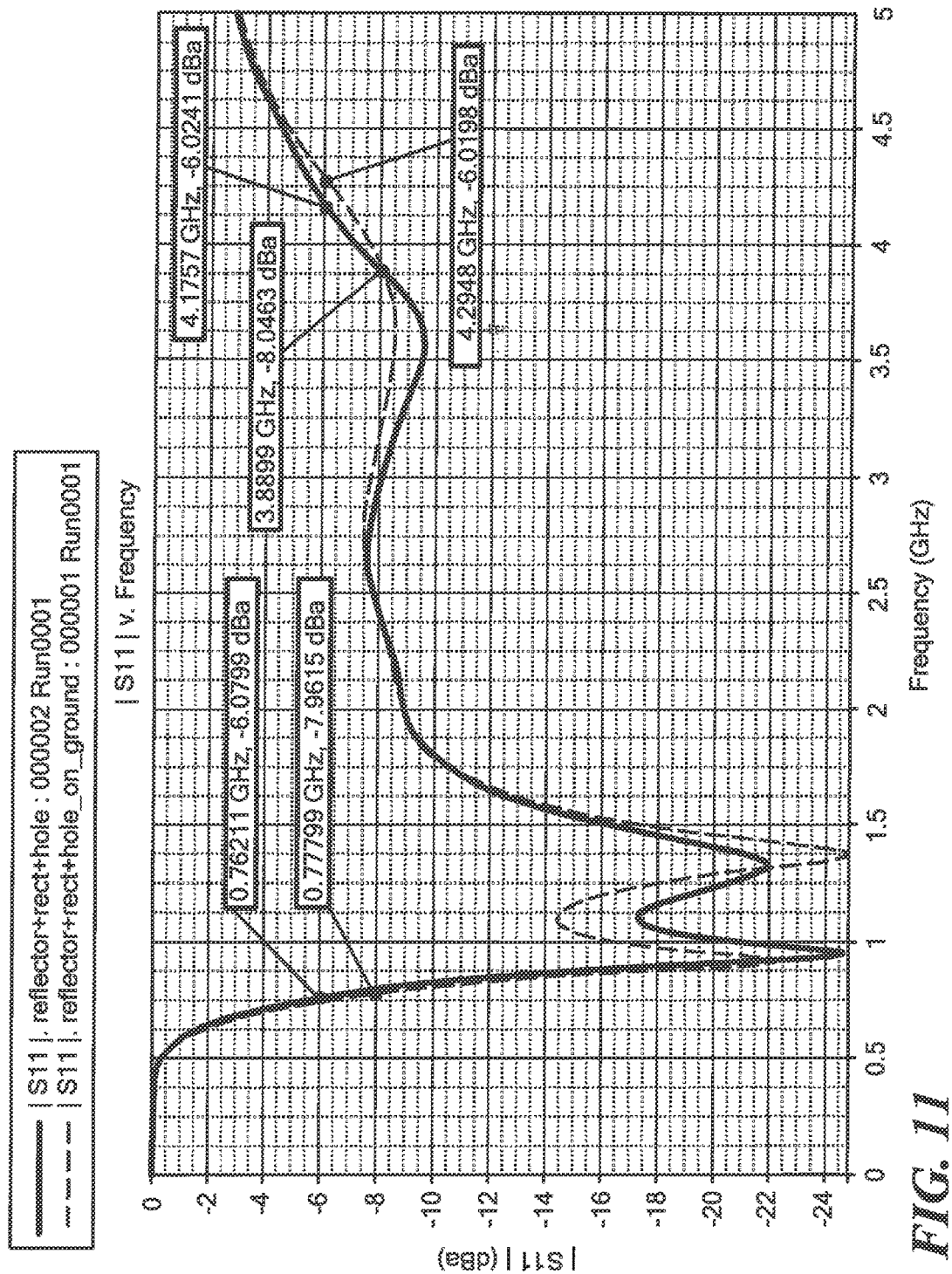
FIG. 11 is a plot illustrating simulated return loss for the antenna of FIG. 9.
Figure 12:
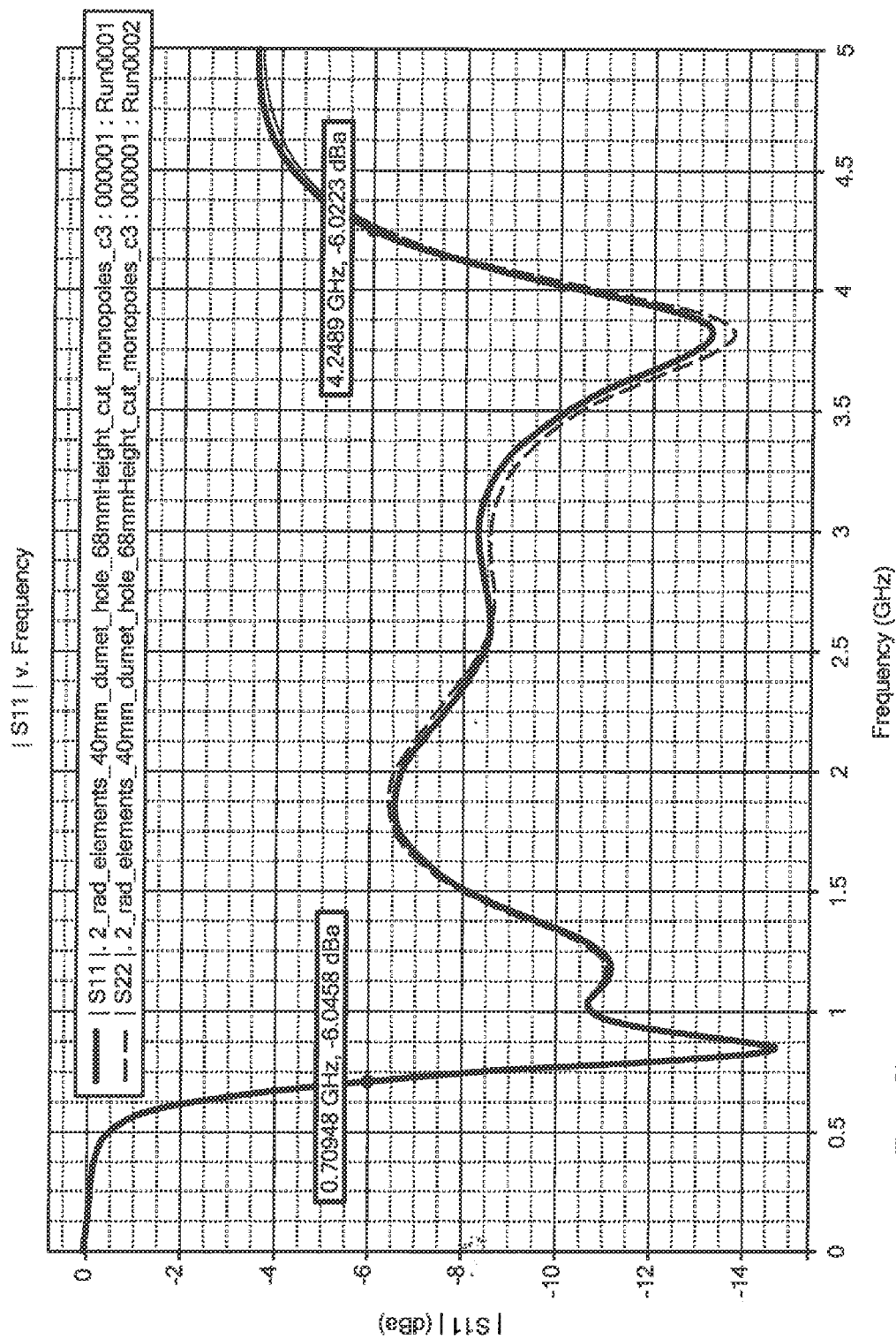
FIG. 12 is a plot illustrating simulated return loss for the antenna of FIG. 10.

FIG. 11 is a plot illustrating simulated return loss versus frequency for the monopole elements 86, 88 of the antenna 80 of FIG. 9 having openings 90, 92 therein. As shown, the elements 86, 88 maintain a return loss of −6 dBa or better for a frequency range from approximately 0.76 GHz to approximately 4.18 GHz. The overall performance is worse than the performance shown in FIG. 8 for the antenna 50 of FIG. 7, but is still sufficient for many applications. FIG. 12 is a plot illustrating simulated return loss for the monopole elements 97, 98 of the antenna 94 of FIG. 10. As shown, the elements 97, 98 maintain a return loss of −6 dBa or better for a frequency range from approximately 0.71 GHz to approximately 4.25 GHz. Thus, the bandwidth of the antenna 94 of FIG. 10 is wider than that of the antenna 80 of FIG. 9.

Figure 13:
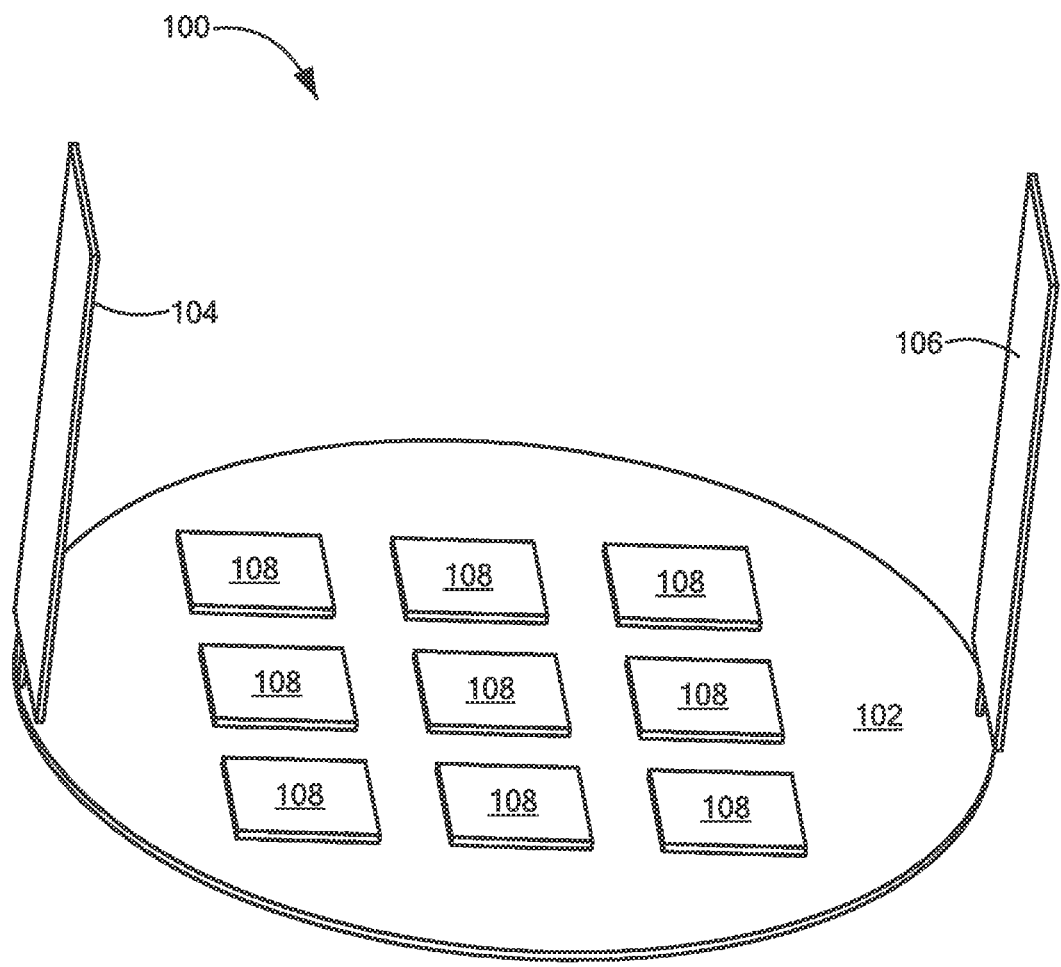
FIG. 13 is a diagram illustrating an exemplary antenna system having a separate array antenna on a ground plane between monopole elements in accordance with an embodiment.

In some embodiments described above, an opening was used in a ground plane shared by multiple monopole elements to implement a collocated optical system. In other embodiments, a ground plane region between monopole elements may be used to implement other RF transducer systems. For example, FIG. 13 is a diagram illustrating an exemplary antenna system 100 that uses such a region to implement a phased array antenna in accordance with an embodiment. As shown, the antenna system 100 includes: a ground plane 102, first and second monopole radiating elements 104, 106, and a plurality of patch radiating elements 108 arranged in a grid configuration. All of the elements 104, 106, 108 utilize the ground plane 108 to facilitate RF transmission and/or reception operation. The array antenna formed by the elements 108 is a separate antenna from the antenna having monopole elements 104, 106. The array antenna may, for example, be operative in a different, non-overlapping frequency band. The array antenna may also have a different far field pattern and may support a different function for the underlying platform than the antenna having the monopole elements 104, 106.

Although shown with nine array elements, it should be appreciated that any number of elements may be used in the array in different implementations. Different array element types may also be used in different implementations (i.e., elements other than patches). As described previously, additional monopole elements may also be provided. In some embodiments, an opening (not shown) may be provided in the ground plane 102 in addition to having the array elements 108. For example, the array may be implement to a side of the opening or around the opening. The opening may then be used to facilitate implementation of an optical system as described previously.

Figure 14:
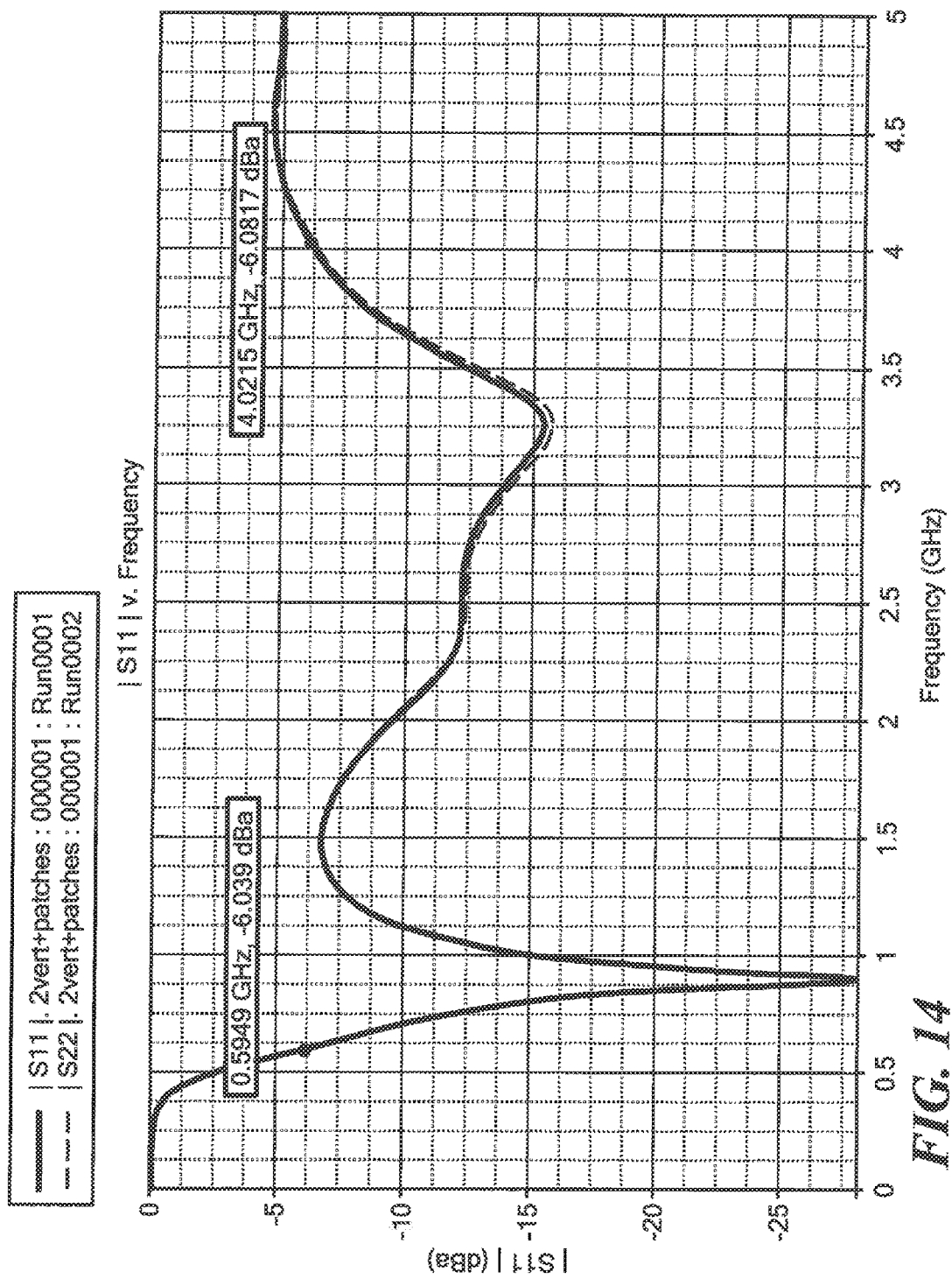
FIG. 14 is a plot illustrating simulated return loss for the antenna of FIG. 13.

FIG. 14 is a plot illustrating simulated return loss versus frequency for the monopole elements 104, 106 of the antenna 100 of FIG. 13, with the array in place. As shown, the elements 104, 106 maintain a return loss of −6 dBa or better for a frequency range from approximately 0.6 GHz to approximately 4.0 GHz.

Figure 15:
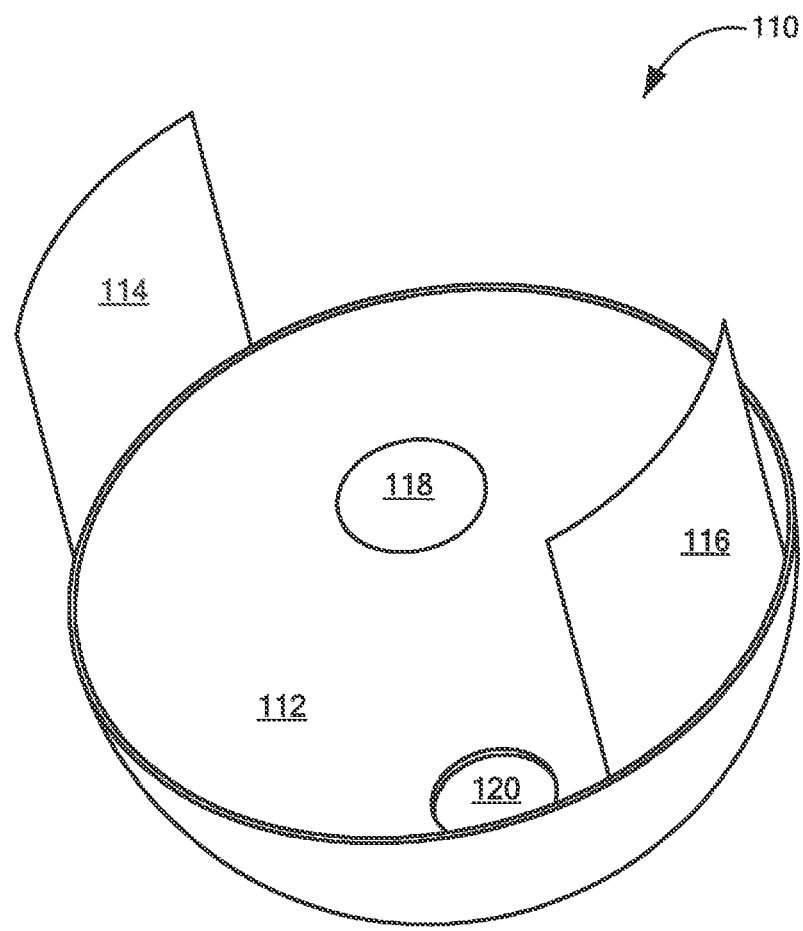
FIG. 15 is a diagram illustrating an exemplary combination RF-optical transducer system that uses a ground plane structure as both an RF ground plane and an optical reflector in accordance with an embodiment.

In the embodiments described above, flat two-dimensional ground planes were used. It was determined, however, that desired performance could still be achieved using non-flat ground plane structures. In addition, it was determined that ground plane structures could be used to perform additional functions in combination RF-optical systems that they were not heretofore used. FIG. 15 is a diagram illustrating an exemplary combination RF-optical transducer system 110 that uses a ground plane structure as both an RF ground plane and an optical reflector in accordance with an embodiment. As shown, the RF-optical transducer system 110 includes: a ground plane 112, first and second monopole radiating elements 114, 116, and a secondary optical reflector 118. As in previous embodiments, the ground plane 112 includes an opening 120 for use in implementing the optical transducer system.

In addition to use as an RF ground structure, the ground plane 112 also operates as a primary optical reflector in the system 110. To operate as an optical reflector, an upper surface of the ground plane 112 can be processed to be more reflective (e.g., highly polished, etc.). Also, the ground plane 112 may have a shape to support the desired reflection. For example, in the embodiment of FIG. 15, the ground plane 112 has a semi-spherical shape. In operation, the optical portion of the RF-optical transducer system 110 may operate like a Cassegrain RF antenna. Thus, to transmit, a light signal may be delivered from a light source behind the ground plane 112, through the opening 120, to a rear side of the secondary reflector 118. The light signal is then reflected back toward the primary reflector/ground plane 112. The primary reflector/ground plane 112 then reflects the signal outward toward an optical element (or optical aperture) in the front of the missile. A light detection operation works in the reverse. The signal is captured by an optical element and directed toward the primary reflector/ground plane. The primary reflector reflects the signal to the secondary reflector which then focuses the light signal through the opening in the ground plane. The signal may then be detected by an optical detector.

The monopole radiating elements 114, 116 operate with the ground plane 112 in substantially the same manner as the monopole elements in the previously described embodiments. It was found that the shape of the ground plane 112 does not significantly degrade RF performance of the monopole elements 114, 116, nor does the highly polished surface. The shape of the monopole elements 114, 116 may follow the curvature of the edge of the ground plane 112 in some implementations. As before, in some embodiments, the monopole elements 114, 116 may conform to a surface of a dielectric radome of a missile. Other techniques for implementing the monopole elements 114, 116 may alternatively be used. Additional monopole elements may also be added to the RF-optical transducer system 110.

The secondary reflector 118 may be held in a central location within a missile nosecone by one or more dielectric supports. In some embodiments, the secondary reflector 118 may be formed of a dielectric material instead of a conductive material to reduce its effect on RF performance. The secondary reflector 118 may be formed of, for example, a meta-material that is designed to be reflective of optical signals but relatively transparent to RF. A metamaterial reflector has to be lossless or near lossless (not lossy) in order to avoid coupling effects with the RF portion of the antenna (e.g., monopoles 114, 116 in FIG. 15). Since the ground plane is metallic/mirror, it will reflect and focus light or infrared (IR) signals on the metamaterial reflector, which in turn will reflect/focus light through the hole/opening 120 of the ground plane 112 of FIG. 15. A metamaterial reflector can be parabolic or flat and combined with another metamaterial lens in order to focus the light through the hole 120. In such a scenario, the metamaterial reflector and the corresponding metamaterial lens should have the same focusing effect. These metamaterial structures can include various layers of dielectric materials with varied refractive indexes arranged in such a way that light/IR gradually bends backwards (reflected basically). This is a similar phenomenon to the troposphere layers, where RF signals bend back to the Earth through the various layers of troposphere.

Design techniques for metamaterial structures having desired qualities are well known in the art. In one popular approach, highly computational electromagnetic (EM) design tools may be used to accurately design such reflectors and reflector/lens combinations. In some implementations, finite difference time domain (FITID) techniques may be used to generate metamaterial secondary reflectors and reflector/lens combinations (e.g., XFDTD EM simulation software from REMCOM, etc.). One textbook that may be used to support metamaterial design is "Metamaterials: Theory, Design and Applications," edited by Tie Jun Cui et al., Springer, New York, 2010.

As described above, the meta-material secondary reflector in combination with the opening in the ground plane allows light focusing without necessarily increasing the aperture in the front. Once the light goes through the hole, then amplification and other processing can be performed. In principle, it is best to avoid the use of too much hardware or active devices in the antenna region because of coupling issues. Higher levels of optical processing may be performed on the opposite side of the ground plane from the antennas. This allows the radome to be sharper (i.e., more pointed) in the front, instead of semi-spherical, which facilitates higher missile speeds. In addition, optical range may be increased because of the increase in light intensity.

Figure 16:
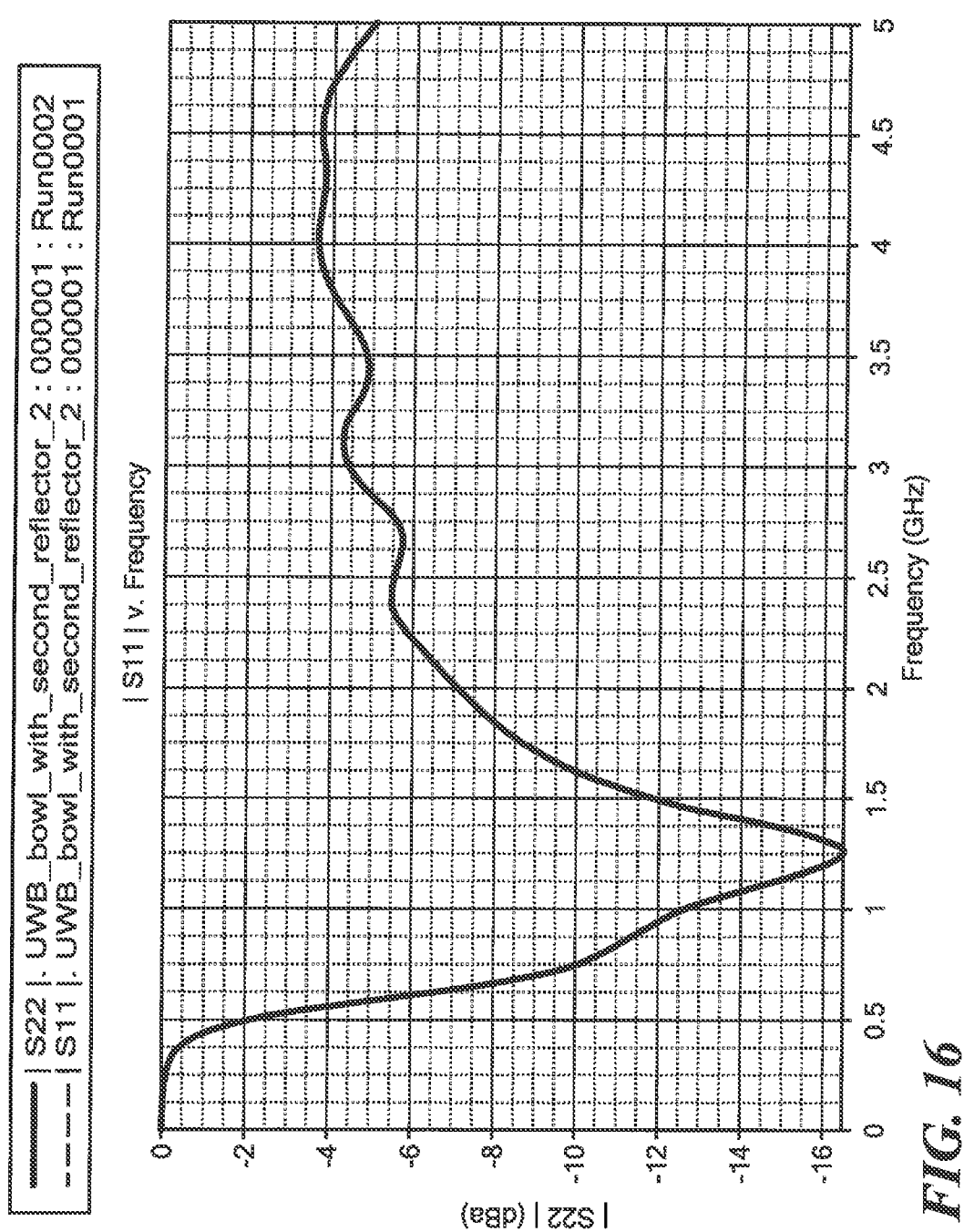
FIG. 16 is a plot illustrating simulated return loss as a function of frequency for the RF-optical transducer system of FIG. 15.

FIG. 16 is a plot illustrating simulated return loss versus frequency for the combination RF-optical transducer system 110 of FIG. 15. As shown, a return loss of −6 dBa or better is achieved over a band from approximately 0.65 GHz to approximately 2.25 GHz. It is believed that this bandwidth could be increased though tuning.

Figure 17:
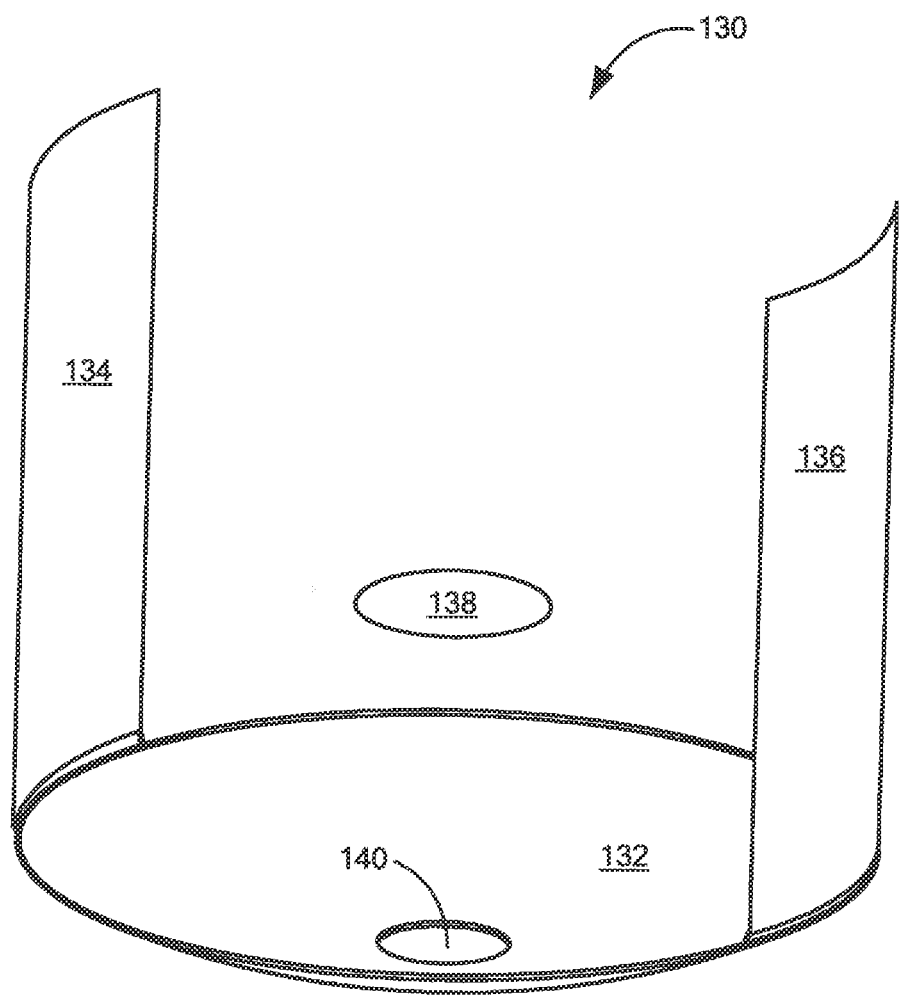
FIG. 17 is a diagram illustrating another exemplary combination RF-optical transducer system that uses a ground plane structure as both an RF ground plane and an optical reflector in accordance with an embodiment.

FIG. 17 is a diagram illustrating an exemplary combination RF-optical transducer system 130 that also uses a ground plane structure as both an RF ground plane and an optical reflector in accordance with an embodiment. As before, the RF-optical transducer system 130 includes: a highly reflective ground plane 132 having an opening 140, first and second monopole radiating elements 134, 136, and a secondary optical reflector 138. However, in this embodiment, the ground plane 132 has a parabolic shape. The transducer system 130 works in substantially the same manner as the one of FIG. 15. The main difference is the shape of the ground plane/reflector 132. The secondary reflector 134 may use meta-materials as described above to reduce coupling with the RF radiating elements.

Figure 18:
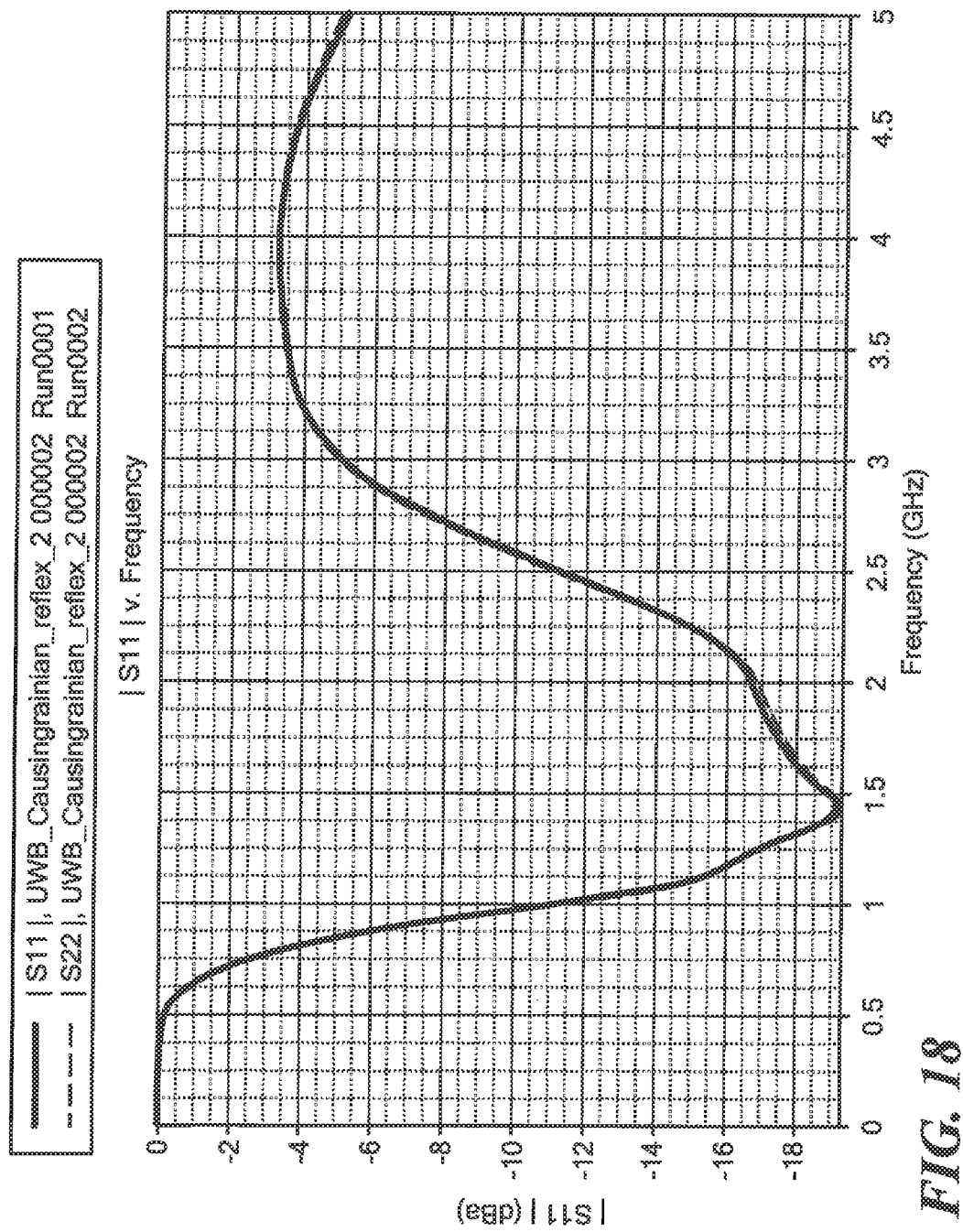
FIG. 18 is a plot illustrating simulated return loss as a function of frequency for the combination RF-optical transducer system of FIG. 17.

FIG. 18 is a plot illustrating simulated return loss versus frequency for the combination RF-optical transducer system 130 of FIG. 17. As shown, a return loss of −6 dBa or better is achieved over a band from approximately 0.8 GHz to approximately 2.7 GHz. It is believed that this bandwidth could be increased though tuning.

Figure 19:
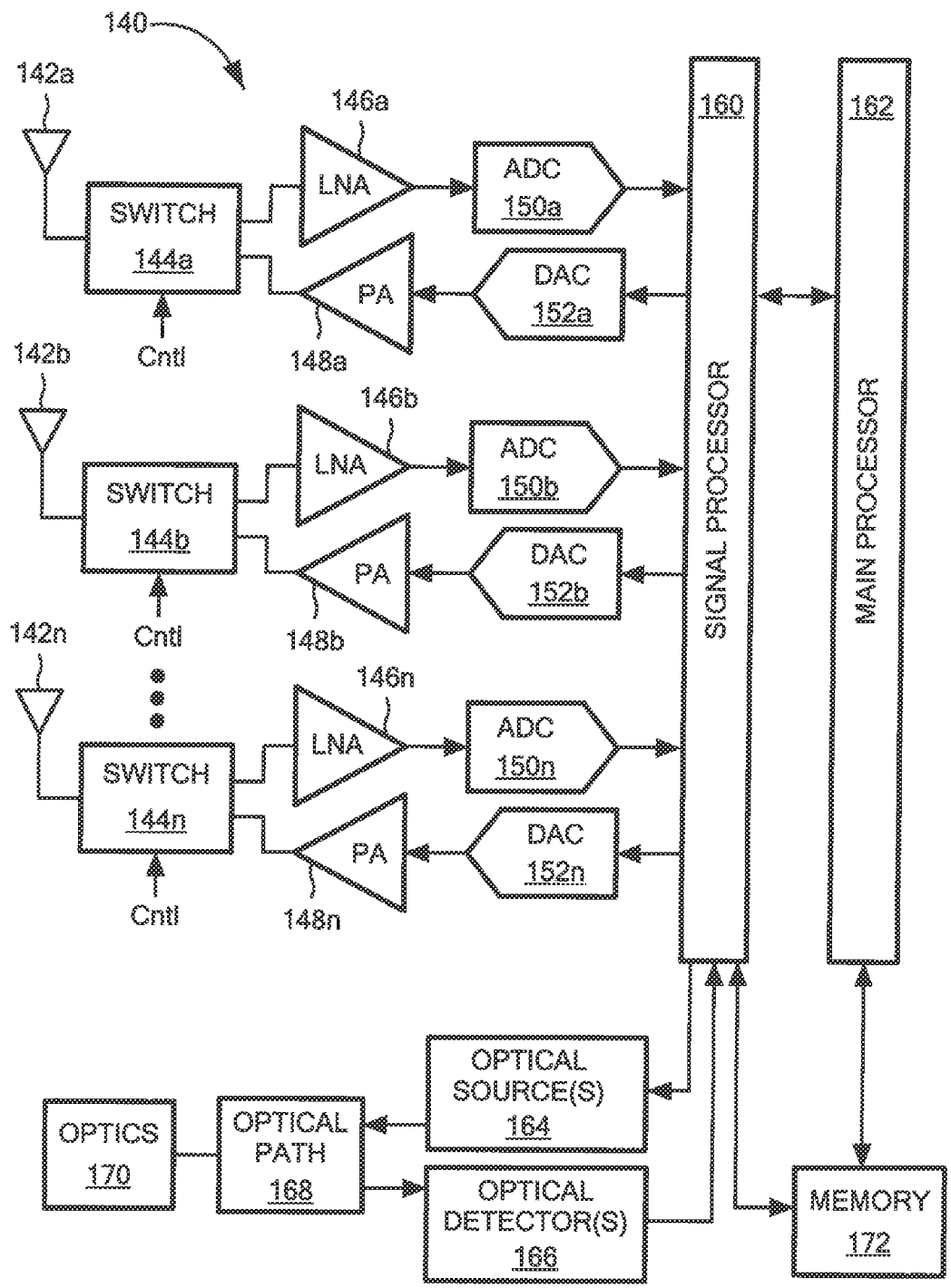
FIG. 19 is a block diagram illustrating exemplary processing circuitry that may be used with one or more of the RF-optical transducer systems described herein.

FIG. 19 is a block diagram illustrating exemplary processing circuitry 140 that may be used with one or more of the combination RF-optical transducer systems described herein. It should be appreciated that the circuitry 140 of FIG. 19 represents one example processing architecture that may be used in different embodiments. Other processing architectures may alternatively be used. As illustrated, the processing circuitry 140 may include: a plurality of radiating elements 142a, 142b, . . . , 142n; a plurality of duplexer switches 144a, 144b, . . . , 144n; a plurality of low noise amplifiers (LNAs) 146a, 146b, . . . , 146n; a plurality of power amplifiers (PAs) 148a, 148b, . . . , 148n; a plurality of analog-to-digital converters (ADCs) 150a, 150b, . . . , 150n; a plurality of digital-to-analog converters (DACs) 152a, 152b, . . . , 152n; a signal processor 160; a main processor 162; one or more optical sources 164; one or more optical detectors 166; an optical path 168, and one or more optical elements 170. The radiating elements 142a, 142b, . . . , 142n represent monopole elements such as those described in various embodiments herein. As described previously, any number of monopole elements may be used in different implementations. Preferably, the monopole elements are provided in pairs that are situated on opposing sides of an underlying ground plane.

In the embodiment shown, the radiating elements 142a, 142b, . . . , 142n operate as both transmit and receive elements. In some embodiments, the radiating elements may operate as transmit only elements or receive only elements. In these embodiments, appropriate changes may be made to the processing circuitry.

The duplexer switches 144a, 144b, . . . , 144n are switches that allow the corresponding radiating elements 142a, 142b, . . . , 142n to be switched between transmit and receive operation. The switches 144a, 144b, . . . , 144n may be controlled by a controller in the system (e.g., main processor 162, etc.). Other types of duplexer structures may alternatively be used. The LNAs 146a, 146b, . . . , 146n provide high gain, low noise amplification to receive signals during receive operations. The ADCs 150a, 150b, . . . , 150n convert the amplified receive signals to a digital representation so that the signals can be digitally processed by the signal processor 160. The signal processor 160 may perform digital downconversion on the digitized receive signals to downconvert the signals to a baseband representation. The signal processor 160 may then process the digital baseband signals in a desired manner. In an alternative arrangement, analog downconversion may be performed before the receive signals reach the ADCs 150a, 150b, . . . , 150n. A combination of analog and digital downconversion may also be used.

During RF transmit operations, the signal processor 160 may provide digital transmit signals to the DACs 152a, 152b, . . . , 152n. The DACs 152a, 152b, . . . , 152n convert the transmit signals to an analog representation. The analog transmit signals are then amplified by the power amplifiers 148a, 148b, . . . , 148n before being transmitted from the 142a, 142b, . . . , 142n. Although not shown, analog upconversion circuitry may be provided between the DACs 152a, 152b, . . . , 152n and the corresponding power amplifiers 148a, 148b, . . . , 148n in some implementations.

The signal processor 160 may be configured to process the transmit and receive signals to achieve one or more desired results. In some embodiments, for example, the signal processor 160 may be configured to perform MIMO processing for transmit and or receive signals. In other embodiments, digital beamforming may be supported. In others, monopulse radar operation may be supported. Similarly, target detection and tracking processing may be supported. Multiple different functions may be supported by the signal processor 160 in some embodiments. The main processor 162 may provide control functions for the signal processor 160 and may facilitate the performance of one or more of the above-described functions.

The signal processor 160 and the main processor 162 may be implemented within one or more digital processing devices. The digital processing device(s) may include, for example, a general purpose microprocessor, a digital signal processor (DSP), a reduced instruction set computer (RISC), a complex instruction set computer (CISC), an application specific integrated circuit (ASIC), a field programmable gate array (FPGA), a programmable logic array (PLA), a microcontroller, an embedded controller, a multi-core processor, a processor complex, and/or others, including combinations of the above. Memory 172 is representative of digital storage within the system and may be used to store, for example, programs, routines, and/or data for the signal processor 160 and the main processor 162. Any type of memory, data storage, or combination thereof may be used.

The optical source(s) 164, optical detector(s) 166, optical path 168, and optics 170 form an optical transducer system that is collocated with the antenna system described above. The optical source(s) 164 may be used during optical signal transmission operations and the optical detector(s) 166 may be used during optical signal reception operations. In some alternative embodiments, optical transmission alone or optical reception alone may be supported.

The optical source(s) 164 is operative for generating light signals for transmission from the RF-optical transducer system. The optical source(s) 164 may generate the light signal based on a signal received from signal processor 160. Any type of light source capable of the required range may be used (e.g., a laser, a laser diode, etc.). During light transmission, the optical path 168 carries the generated light signals to the optics 170 for transmission. The optical path 168 may include a fiber optic cable or other optical medium or media. The optical path 168 may also include one or more unobstructed sections of air through which a light signal can travel and/or various reflector units for reflecting light signals. The optics 170 may include one or more lenses or other optical elements for launching a light signal into space.

During light signal reception, the optics 170 may capture a light signal from space and focus the signal onto or into the optical path 168. The path 168 then carries the signal to the optical detector(s) 166 for detection. The detected signal may then be delivered to the signal processor 160 to be processed. The signal processor 160 and/or the main processor 162 may be configured to implement one or more optical functions of interest.

As described previously, in some embodiments, combination RF-optical transducer systems are provided that include a ground plane having an opening therein. In these embodiments, the optical transducer system described above may extend through the opening in the ground plane. More specifically, any one or more of the optics 170, the optical path 168, the optical source(s) 164, or the optical detector(s) 166 of FIG. 19 may be located within or extend through the opening in the ground plane. In some embodiments, the ground plane may also act as an optical reflector and thus form a part of the optical path. In some embodiments, the optical source(s) 164 and the optical detector(s) 166 may be located behind the ground plane and the optical path 168 may extend through the opening in the ground plane to connect to the optics 170. Other arrangements may alternatively be used.

Figure 20A:
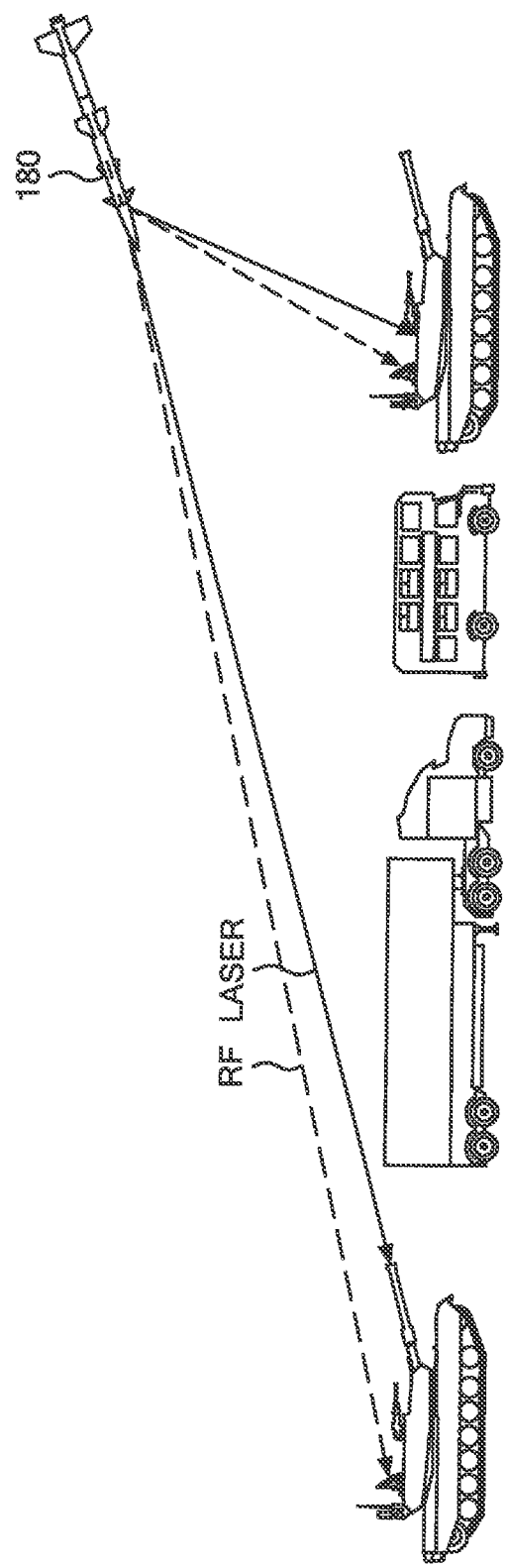
FIGS. 20a and 20b are diagrams illustrating some missile applications that may make use of RF/optical transducer system described herein.
Figure 20B:
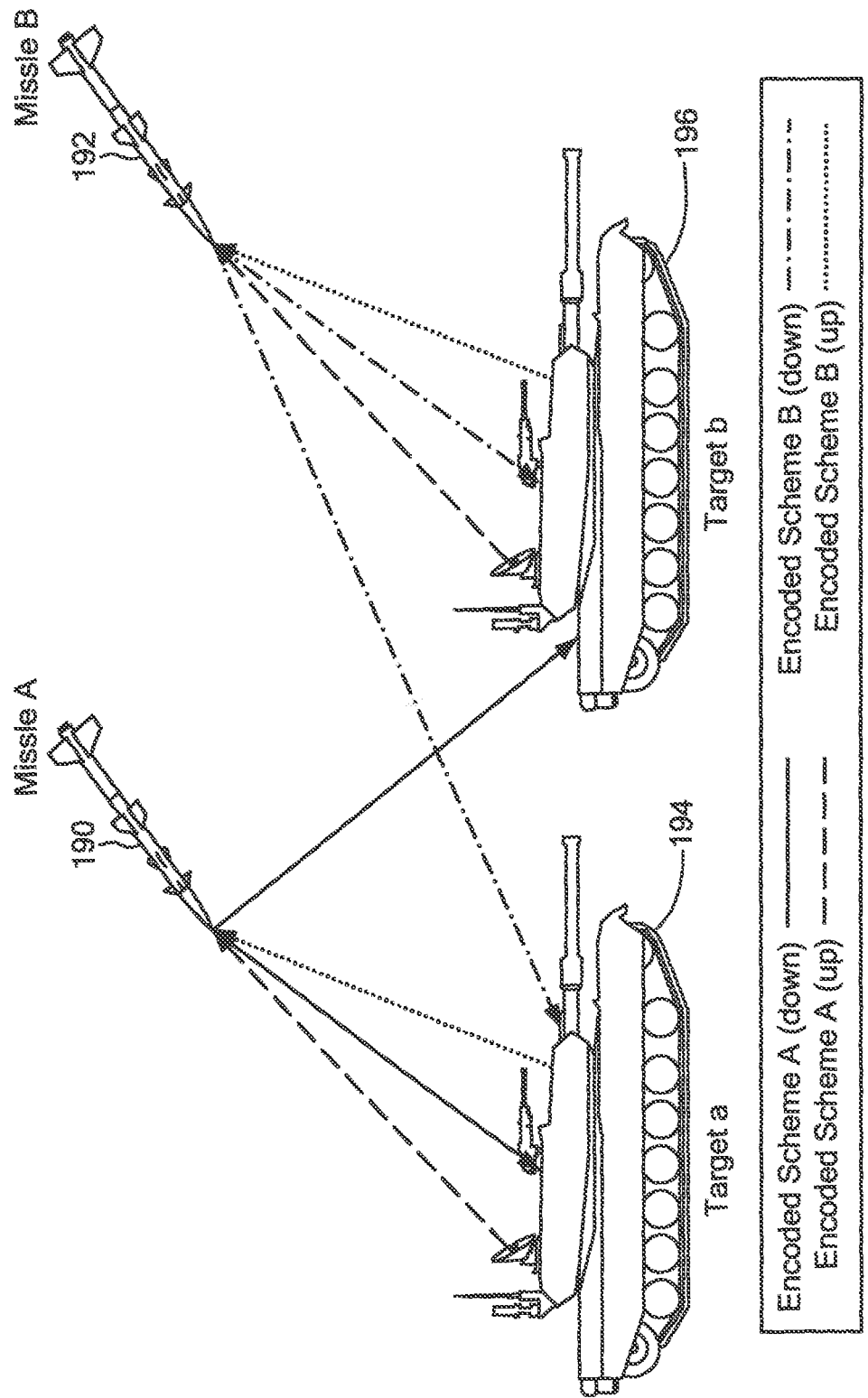

FIGS. 20*a* and 20*b* are diagrams illustrating some missile applications that may make use of a combination RF/optical system in accordance with embodiments disclosed herein. FIG. 20*a* illustrates a scenario involving a missile 180 having a semi-active laser seeker integrated therein to allow for designation of a specific target that the RF guided missile should strike. The optical subsystem in this arrangement thus increases the precision of the guidance, allowing flexible and fast reaction targeting. FIG. 20*b* illustrates a scenario where there are multiple missiles 190, 192 and multiple targets 194, 196. In this scenario, target discrimination may be achieved by using different optical encoding schemes per missile and per target so that the two missiles 190, 192 do not hit the same target. The various RF/optical systems described herein may be used to carry out this optical target discrimination technique.

Although described above primarily in the context of missile applications, it should be understood that many of the described concepts, features, structures, systems, and techniques may also be used in other applications. These applications include, for example, cellular base stations, subscriber stations, global positioning system (GPS) radios, radar systems, communication data links, and others.

Elements of different embodiments described herein may be combined to form other embodiments not specifically set forth above. Various elements, which are described in the context of a single embodiment, may also be provided separately or in any suitable sub-combination. Other embodiments not specifically described herein are also within the scope of the following claims.

Having described exemplary embodiments of the invention, it will now become apparent to one of ordinary skill in the art that other embodiments incorporating their concepts may also be used. The embodiments contained herein should not be limited to disclosed embodiments but rather should be limited only by the spirit and scope of the appended claims. All publications and references cited herein are expressly incorporated herein by reference in their entirety.

What is claimed is:

1. A transducer system comprising:
an antenna subsystem including multiple radio frequency (RF) radiating elements disposed adjacent to a ground plane, wherein the multiple RF radiating elements include first and second monopole radiating elements located near opposing edges of the ground plane; and
an optical transducer subsystem collocated with the antenna subsystem, wherein the round plane is an optical reflector in the optical transducer subsystem in addition to being a ground plane in the antenna subsystem.

2. The transducer system of claim 1, wherein:
the ground plane includes an opening in a central region thereof; and
the optical transducer subsystem extends through the opening in the ground plane.

3. The transducer system of claim 1, wherein:
the optical transducer subsystem includes an optical source to generate a light signal, an optical element to transmit the light signal into an exterior environment, and an optical path coupling the optical source and the optical element, wherein the ground plane is an optical reflector within the optical path.

4. The transducer system of claim 1, wherein:
the ground plane is a primary optical reflector within an optical path of the optical transducer subsystem; and
the optical transducer subsystem further comprises a secondary optical reflector within the optical path that is different from the primary optical reflector.

5. The transducer system of claim 4, wherein:
the secondary optical reflector is formed of dielectric material.

6. The transducer system of claim 4, wherein:
the secondary optical reflector is formed of meta-material.

7. The transducer system of claim 4, wherein:
the ground plane includes an opening in a central region thereof; and
the secondary reflector is positioned to focus light signals through the opening in the ground plane during light signal reception operations.

8. The transducer system of claim 1, wherein:
the ground plane has either a parabolic shape or a semispherical shape.

9. The transducer system of claim 1, wherein:
the ground plane is highly polished.

10. The transducer system of claim 1, wherein:
the ground plane has a highly reflective coating.

11. The transducer system of claim 1, wherein:
the first and second monopole radiating elements each include an opening therein for use as an optical aperture.

12. The transducer system of claim 1, wherein:
the transducer system is located within a missile.

13. A transducer system comprising:
an antenna subsystem including multiple radio frequency (RF) radiating elements disposed adjacent to a ground plane, wherein the multiple RF radiating elements include first and second monopole radiating elements located near opposing edges of the ground plane;
an optical transducer subsystem collocated with the antenna subsystem, wherein the round plane is an optical reflector in the optical transducer subsystem in addition to being a ground plane in the antenna subsystem;
wherein the ground plane is a primary optical reflector within an optical path of the optical transducer subsystem, the optical transducer subsystem further comprises a secondary optical reflector within the optical path that is different from the primary optical reflector; and
the secondary optical reflector is located in a region between the first and second monopole radiating elements, wherein the secondary optical reflector provides little or no coupling with the first and second monopole radiating elements.

14. A transducer system comprising:
an antenna subsystem including multiple radio frequency (RF) radiating elements disposed adjacent to a ground plane, wherein the multiple RF radiating elements include first and second monopole radiating elements located near opposing edges of the ground plane;
the first and second monopole radiating elements are conformal to a surface of a radome; and
an optical transducer subsystem collocated with the antenna subsystem, wherein the round plane is an optical reflector in the optical transducer subsystem in addition to being a ground plane in the antenna subsystem.

15. A transducer system comprising:
an antenna subsystem including:
a ground plane having an opening in a central region thereof; and
a plurality of monopole antenna elements coupled to and projecting above the ground plane; and
an optical transducer subsystem collocated with the antenna subsystem, the optical transducer subsystem including a secondary reflector configured to reflect light signals toward the opening in the ground plane or reflect light signals received through the opening in the ground plane during optical operations; and
a radome disposed about said antenna subsystem and said optical transducer subsystem, and wherein said plurality of monopole antenna elements are integrated into a surface of said radome.

16. The transducer system of claim 15, wherein:
the secondary reflector is located between at least two of the RF radiating elements of the antenna subsystem and is formed of dielectric material to prevent significant coupling with the at least two RF radiating elements.

17. The transducer system of claim 15, wherein:
the secondary reflector includes meta-material.

18. The transducer system of claim 15, wherein:
the ground plane is a primary optical reflector in an optical path associated with the optical transducer subsystem in addition to being a ground plane in the antenna subsystem.

19. The transducer system of claim 18, wherein:
the ground plane has either a parabolic shape or a semispherical shape.

20. The transducer system of claim 15, wherein:
the plurality of monopole antenna elements are disposed on and in contact with the ground plane.

21. The transducer system of claim 15, wherein:
the plurality of monopole antenna elements are integrated onto a surface of the ground plane.

* * * * *